(12) United States Patent
Hasegawa et al.

(10) Patent No.: US 6,743,178 B2
(45) Date of Patent: Jun. 1, 2004

(54) NONINVASIVE CONTINUOUS BLOOD PRESSURE MEASURING APPARATUS AND A METHOD OF NONINVASIVELY MEASURING CONTINUOUS BLOOD PRESSURE

(75) Inventors: Kinya Hasegawa, Sagamihara (JP); Yushi Nishimura, Yokohama (JP); Hisashi Hagiwara, Yokohama (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 10/057,910

(22) Filed: Jan. 29, 2002

(65) Prior Publication Data

US 2002/0169380 A1 Nov. 14, 2002

Related U.S. Application Data

(62) Division of application No. 09/290,394, filed on Apr. 13, 1999, now Pat. No. 6,358,212.

(30) Foreign Application Priority Data

| Apr. 20, 1998 | (JP) | ............................................. | 10-123892 |
| May 13, 1998 | (JP) | ............................................. | 10-146668 |
| May 13, 1998 | (JP) | ............................................. | 10-146669 |
| Jun. 1, 1998 | (JP) | ............................................. | 10-165839 |

(51) Int. Cl.[7] ................................................. A61B 5/00
(52) U.S. Cl. ....................................... 600/485; 600/500
(58) Field of Search ................................. 600/485, 490, 600/500, 453–6

(56) References Cited

U.S. PATENT DOCUMENTS

| 3,090,377 A | 5/1963 | Salisbury |
| 3,095,872 A | 7/1963 | Tolles |
| 5,273,046 A | 12/1993 | Butterfield et al. |
| 5,590,649 A | 1/1997 | Caro et al. |
| 5,830,131 A | 11/1998 | Caro et al. |
| 5,904,654 A | 5/1999 | Wohltmann et al. |

FOREIGN PATENT DOCUMENTS

| WO | WO 86/04801 | 8/1986 |
| WO | WO 95/28126 | 10/1995 |
| WO | WO 97/14355 | 4/1997 |
| WO | WO 97/49328 | 12/1997 |

OTHER PUBLICATIONS

Shimazu et al.: "Vibration technique for indirect measurement of diastolic arterial pressure in human fingers"Medical & Biological Engineering & Computing, vol. 27, No. 2, Mar. 1989, pp. 130–136, XP000071965.

*Primary Examiner*—Robert L. Nasser
(74) *Attorney, Agent, or Firm*—Connolly Bove Lodge & Hutz LLP

(57) ABSTRACT

One of pairs of an exciter and a sensor is selected in accordance with the detection signal which is derived from an exciter waveform induced in an artery transmitted therethrough. The pairs of exciters and sensors are arranged on a substrate in various formations. A/D converters are provided to respective detection signals. A frequency of the oscillation signal supplied to the exciter is controlled by various oscillation signal generation circuits. Bandpass filtering for extracting the exciter waveform, low-pass-filtering for extracting a natural blood pressure waveform, phase difference detection processes are provided by a microprocessor, wherein the bandpass filtering and low-pass-filtering processes may be replaced with a bandpass filter and a low pass filter, and their outputs are selected by a switching circuit and supplied to the microprocessor through one a/d converter. The frequency of the oscillation signal is controlled to an optimum frequency by detecting the detection signal and estimating the attenuation, dispersion, phase shift with respect to different frequency and by determining one of the different frequency in accordance with the estimation result. The waveform of the oscillation signal is controlled to an optimum waveform similarly.

1 Claim, 17 Drawing Sheets

DET SIG 100c

DET SIG 100d

OUTPUT OF MULT 4

OUTPUT OF A/D-C

DETERMINED DET SIG

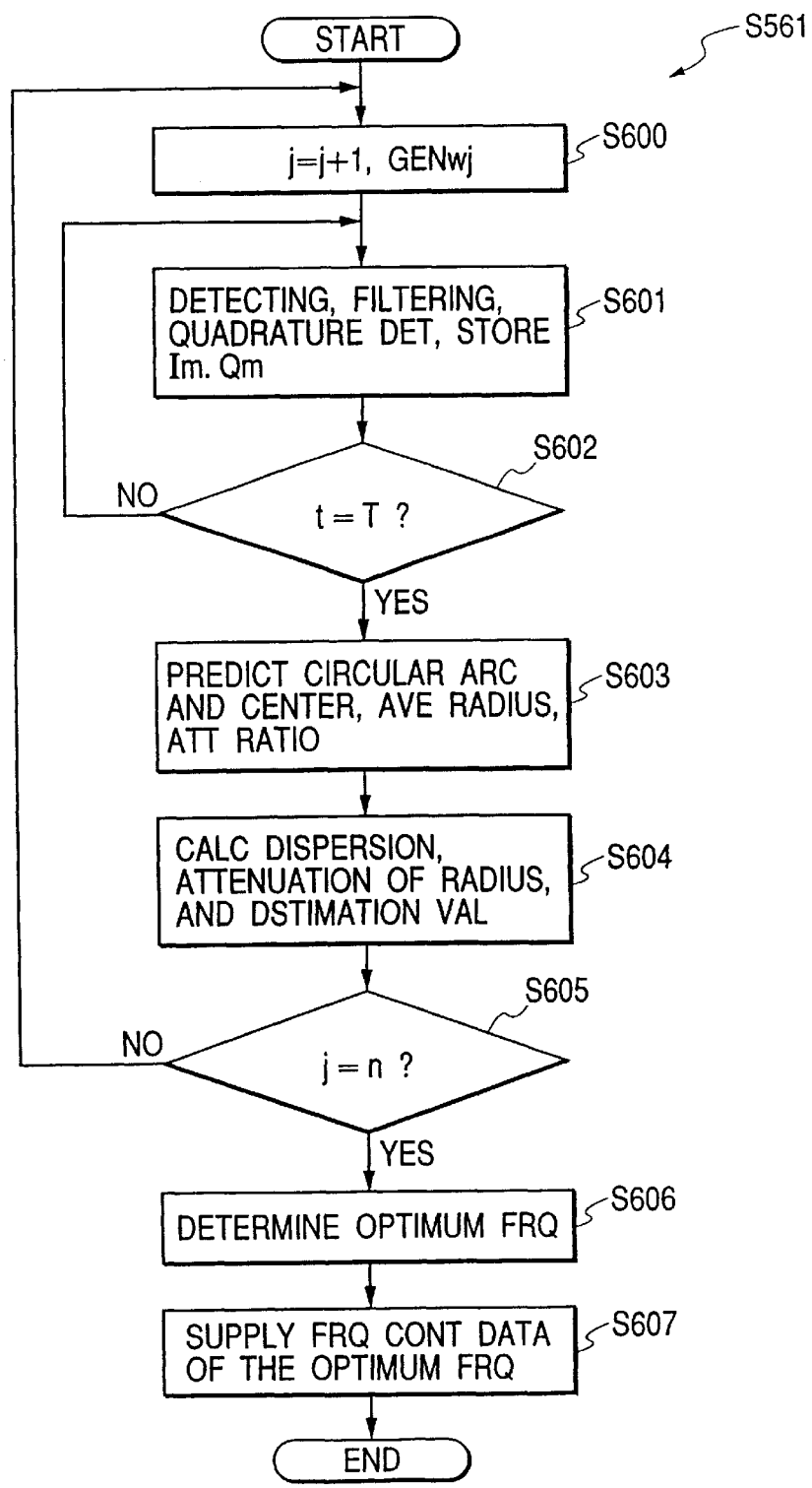

NONINVASIVE CONTINUOUS BLOOD PRESSURE MEASURING APPARATUS AND A METHOD OF NONINVASIVELY MEASURING CONTINUOUS BLOOD PRESSURE

This application is a divisional of U.S. Ser. No. 09/290,394, filed Apr. 13, 1999, now U.S. Pat. No. 6,358,212.

BACKGROUND OF THE INVENTION

1. Field of the Invention

This invention relates to a noninvasive continuous blood pressure measuring apparatus for noninvasively, continuously measuring blood pressure and a method of noninvasively measuring continuous blood pressure.

2. Description of the Prior Art

A noninvasive continuous blood pressure measuring apparatus for noninvasively, continuously measuring blood pressure is known. An apparatus and a method for measuring an induced perturbation to determine a blood pressure is disclosed in U.S. Pat. No. 5,590,649. In this prior art apparatus, a monitor for continuously determining a patient's physiological parameter includes a means for obtaining a periodic calibration measurement of the patient's physiological parameter. An exciter, positioned over an artery of the patient induces an exciter waveform into the patient's arterial blood. A noninvasive sensor, positioned over the artery, senses a hemoparameter and provides a noninvasive sensor signal output representative of the hemoparameter. A processor receives the calibration measurement and noninvasive sensor signal output. The processor determines a SC offset based on the calibration measurement and processes the noninvasive sensor signal to continuously determine the patient's physiological parameter.

SUMMARY OF THE INVENTION

The aim of the present invention is to provide a superior noninvasive continuous blood pressure measuring apparatus and a superior method of noninvasively measuring continuous blood pressure.

According to this invention, there is provided a first noninvasive continuous blood pressure measuring apparatus including: an oscillator for generating an oscillation signal having a desired frequency and a desired amplitude; a substrate; a plurality of exciters arranged on the substrate in a direction responsive to the oscillation signal for inducing exciter waveforms in an artery and a blood in the artery of a living body; a plurality of sensors respectively arranged on the substrate in the direction a predetermined interval apart from the exciters for receiving induced exciter waveforms transmitted through the artery from the living body and outputting detection signals; a multiplexer for effecting recurrently switching and time-divisionally outputting outputs of the sensors; a determining and selecting portion responsive to the multiplexer for determining one of the outputs in accordance with a predetermined judging condition and for selecting and outputting one of the outputs; a calibration hemadynamometer for detecting absolute values of a maximum blood pressure and a minimum blood pressure of the living body; a calculating portion for receiving the absolute values from the hemadynamometer and successively calculating and outputting an instantaneous blood pressure value from a phase relation between the oscillation signal and one of the outputs from the determining and selecting portion and the absolute values; and a display for displaying a continuous blood pressure variation from the instantaneous blood pressure successively outputted by the calculation portion.

In the first noninvasive continuous blood pressure measuring apparatus, the substrate correspondingly arranges the exciters and the sensors such that each pair of each of the exciters and each of the sensors is arranged in the direction and the exciter and the sensor of each pair are arranged in a second direction perpendicular to the direction, the apparatus further including an attaching unit for attaching the substrate to the living body.

In the first noninvasive continuous blood pressure measuring apparatus, the substrate may correspondingly arranges the exciter and the sensors such that each pair including two of the sensors and one of the exciter arranged between the two of the sensors with the predetermined distance is arranged in the direction, the apparatus may further include an attaching unit for attaching the substrate to the living body.

The first noninvasive continuous blood pressure measuring apparatus may further include: a plurality of a/d converters for respectively a/d-converting the detection signals and supplying converted signals to the determining and selecting portion as the outputs of the sensors.

According to this invention, there is a second noninvasive continuous blood pressure measuring apparatus-is provided which includes: an oscillator for generating an oscillation signal having a desired frequency and a desired amplitude; an exciter arranged responsive to the oscillation signal for inducing an exciter waveform in an artery and blood in the artery of a living body; a sensor arranged a predetermined interval apart from the exciter for receiving the induced exciter waveform transmitted through the artery from the living body and outputting a detection signal; a calibration hemadynamometer for detecting absolute values of a maximum blood pressure and a minimum blood pressure of the living body; a calculating portion for receiving absolute values from the calibration hemadynamometer and successively calculating and outputting an instantaneous blood pressure value from a phase relation between the oscillation signal and the detection signal and the absolute values; and a display for displaying a continuous blood pressure variation from the instantaneous blood pressure successively outputted by the calculation portion.

In the second noninvasive continuous blood pressure measuring apparatus, the oscillator may include: a clock signal generation circuit for generating a clock signal; a processor responsive to frequency control data and the clock signal for successively generating frequency signal data indicative of amplitude in time base in accordance with the frequency control data; a d/a converter for converting the frequency signal data; and a filter for low-pass filtering an output of the d/a converter and outputting the oscillation signal of which frequency is controlled in accordance with the frequency data.

In the second noninvasive continuous blood pressure measuring apparatus, the oscillator may include: a clock signal generation circuit for generating a clock signal; a numerically-controlled oscillator responsive to frequency control data and the clock signal for successively generating frequency signal data indicative of amplitude in time base in accordance with the frequency control data; a d/a converter for converting the frequency signal data; and a filter for low-pass filtering an output of the d/a converter and outputting the oscillation signal of which frequency is controlled in accordance with the frequency data.

In the second noninvasive continuous blood pressure measuring apparatus, the oscillator may include: a clock signal generation circuit for generating a clock signal; a processor responsive to frequency control data for generating at least one cycle of frequency signal data and storing one cycle of frequency signal data in a look-up table; an address signal generating circuit for generating an address signal in response to the clock signal to operate the look-up table to successively read and output one cycle of frequency data indicative of an amplitude of the oscillation signal; a d/a converter for converting one cycle of frequency data; and a filter for low-pass filtering an output of the a/d converter and outputting the oscillation signal of which frequency is controlled in accordance with the frequency data.

In the second noninvasive continuous blood pressure measuring apparatus, the oscillator may include: a PLL circuit responsive to frequency control data for successively generating a frequency signal; and a filter for low-pass filtering the frequency signal and outputting the filtered frequency signal as the oscillation signal of which frequency is controlled in accordance with the frequency data.

According to this invention, there is provided a third noninvasive continuous blood pressure measuring apparatus which includes: an oscillator for generating an oscillation signal having a desired frequency and a desired amplitude; an exciter responsive to the oscillation signal for inducing an exciter waveform in an artery and blood in the artery of a living body; a sensor arranged a predetermined interval apart from the exciter for receiving the induced exciter waveform transmitted through the artery from the living body and outputting a detection signal; an aid converter for a/d-converting the detection signal; a calibration hemadynamometer for detecting absolute values of a maximum blood pressure and a minimum blood pressure of the living body; a microprocessor including a filter portion and a calculating portion, the filter portion band-pass-filtering the detection signal from the a/d converter, the calculating portion receiving the absolute values from the calibration hemadynamometer and successively calculating and outputting an instantaneous blood pressure value from a phase relation between the oscillation signal and the detection signal from the filter portion and the absolute values; and a display for displaying a continuous blood pressure variation from the instantaneous blood pressure successively outputted by the calculation portion.

According to this invention, there is provided a fourth noninvasive continuous blood pressure measuring apparatus which includes: an oscillator for generating an oscillation signal having a desired frequency and a desired amplitude; an exciter responsive to the oscillation signal for inducing an exciter waveform in an artery and-a blood in the artery of a living body; a sensor arranged a predetermined interval apart from the exciter for receiving the induced exciter waveform transmitted through the artery from the living body and outputting a detection signal; a calibration hemadynamometer or detecting absolute values of a maximum blood pressure and a minimum blood pressure of the living body; a bandpass filter for band-pass-filtering the detection signal from the sensor, an a/d converter for a/d-converting the detection signal from the bandpass filter; a microprocessor including a calculating portion for receiving the absolute values from the calibration hemadynamometer and successively calculating and outputting an instantaneous blood pressure value from a phase relation between the oscillation signal and the detection signal from the a/d converter and the absolute values; and a display for displaying a continuous blood pressure variation from the instantaneous blood pressure successively outputted by the calculation portion.

According to this invention, there is provided a fifth noninvasive continuous blood pressure measuring apparatus which includes: an oscillator for generating an oscillation signal of which frequency is controlled; an exciter responsive to the oscillation signal for inducing an exciter waveform in an artery and blood in the artery of a living body; a sensor arranged a predetermined interval apart from the exciter for receiving the induced exciter waveform transmitted trough the artery from the living body and outputting a detection signal; a calibration hemadynamometer for detecting absolute values of a maximum blood pressure and a minimum blood pressure of the living body; a frequency determining portion responsive to-the sensor for controlling the oscillator to successively control the frequency at different frequencies and determining one of the difference frequencies in accordance with the detection signal outputted at different frequencies, and then, controlling the oscillator to continuously generate the oscillation signal at one of the different frequencies; a calculating portion responsive to the frequency determining portion for receiving absolute values from the calibration hemadynamometer and successively calculating and outputting an instantaneous blood pressure value from a phase relation between the oscillation signal and the detection signal at one of the different frequencies and the absolute values; and a display for displaying a continuous blood pressure successively outputted by the calculation portion.

In the fifth noninvasive continuous blood pressure measuring apparatus, the frequency determining portion may detect attenuations in the detection signal at different frequencies and determine one of the difference frequencies in accordance with a minimum of the attenuations.

In the fifth noninvasive continuous blood pressure measuring apparatus, the frequency determining portion may detect dispersions in amplitudes of the detection signal at different frequencies and determine one of the different frequencies in accordance with a minimum of the dispersions.

In the fifth noninvasive continuous blood pressure measuring apparatus, the frequency determining portion may detect phase shifts in the detection signal at different frequencies and determine one of the difference frequencies in accordance with a maximum of the phase shifts.

In the fifth noninvasive continuous blood pressure measuring apparatus, the frequency determining portion may detect attenuations in the detection signal at different frequencies, detect dispersions in amplitudes of the detection signal at the different frequencies, and detect phase shifts in the detection signal at the different frequencies, obtain estimation values at the different frequencies through an estimating function for estimating the attenuations, the dispersions, and the phase shifts, and determine one of the difference frequencies in accordance with the estimation values at the different frequencies.

According to this invention, there is provided a sixth noninvasive continuous blood pressure measuring apparatus which includes: an oscillator for generating an oscillation signal of which waveform is controlled an exciter responsive to the oscillation signal for inducing an exciter waveform in an artery and-a blood in the artery of a living body; a sensor arranged a predetermined interval apart from the exciter for receiving the induced exciter waveform transmitted through the artery from the living body and outputting a detection signal; a calibration hemadynamometer for detecting absolute values of a maximum blood pressure and a minimum blood pressure of the living body; a waveform determining portion responsive to the sensor for controlling the oscillator to control the oscillation signal successively have different waveforms and determining one of the difference waveforms in accordance with the detection signal outputted at different waveforms and then, controlling the oscillator to continuously generate the oscillation signal at one of the different waveforms; a calculating portion responsive to the frequency determining portion for receiving absolute values from the calibration hemadynamometer and successively calculating and outputting an instantaneous blood pressure value from a phase relation between the oscillation signal and the detection signal at one of the different waveforms and the absolute values; and a displaying for displaying a continuous blood pressure variation from the instantaneous blood pressure successively outputted by the calculation portion.

In the sixth noninvasive continuous blood pressure measuring apparatus, the waveform determining portion may detect attenuations in the detection signal at the different waveforms and determine one of the difference waveforms in accordance with a minimum of the attenuations.

In the sixth noninvasive continuous blood pressure measuring apparatus, the waveform determining portion may detect dispersions in amplitudes of the detection signal at the different waveforms and determines one of the difference waveforms in accordance with a minimum of the dispersions.

In the sixth noninvasive continuous blood pressure measuring apparatus, the waveform determining portion may detect phase shifts in the detection signal at the different waveforms and determine one of the difference waveforms in accordance with a maximum of the phase shifts.

In the sixth noninvasive continuous blood pressure measuring apparatus, the waveform determining portion may detect attenuations in the detection signal at the different waveforms, detect dispersions in amplitudes of the detection signal at the different waveforms, and detect phase shifts in the detection signal at the different waveforms, obtain estimation values at the different waveforms through an estimating function for estimating the attenuations, the dispersions, and the phase shifts, and determine one of the difference waveforms in accordance with the estimation values at the different waveforms.

According to this invention, there is provided a first method of noninvasively measuring continuous blood pressure including the steps of; generating an oscillation signal of which frequency is controlled; providing an exciter responsive to the oscillation signal inducing an exciter waveform in an artery and blood in the artery of a living body; providing a sensor arranged a predetermined interval apart from the exciter for receiving the induced exciter waveform transmitted trough the artery from the living body and outputting a detection signal; detecting absolute values of a maximum blood pressure and a minimum blood pressure of the living body; controlling the oscillation signal to successively control the frequency at different frequencies and determining one of the difference frequencies in accordance with the detection signal outputted at different frequencies; continuously generating the oscillation signal at one of the different frequencies; receiving absolute values and successively calculating and outputting an instantaneous blood pressure value from a phase relation between the-oscillation signal and the detection signal at one of the different frequencies and the absolute values; and displaying a continuous blood pressure variation from the instantaneous blood pressure successively outputted.

According to this invention, there is provided a second method of noninvasively measuring continuous blood pressure including the steps of: generating an oscillation signal of which waveform is controlled; providing an exciter responsive to the oscillation signal inducing an exciter waveform in an artery and blood in the artery of a living body; providing a sensor arranged a predetermined interval apart from the exciter for receiving the induced exciter waveform transmitted through the artery from the living body and outputting a detection signal; detecting absolute values of a maximum blood pressure and a minimum blood pressure of the living body; controlling the oscillation signal to successively control the frequency at different waveforms and determining one of the difference waveforms in accordance with the detection signal outputted at different waveforms; continuously generating the oscillation signal at one of the different waveforms; receiving absolute values and successively calculating and outputting an instantaneous blood pressure value from a phase relation between the oscillation signal and the detection signal at one of the different waveforms and the absolute values; and displaying a continuous blood pressure variation from the instantaneous blood pressure successively outputted.

BRIEF DESCRIPTION OF THE DRAWINGS

The object and features of the present invention will become more readily apparent from the following detailed description taken in conjunction with the accompanying drawings in which:

FIG. 21 depicts a flow chart of the eleventh embodiment showing an operation of the waveform determining portion.

The same or corresponding elements or parts are designated with like references throughout the drawings.

DETAILED DESCRIPTION OF THE INVENTION (FIRST EMBODIMENT)

Figure 1:
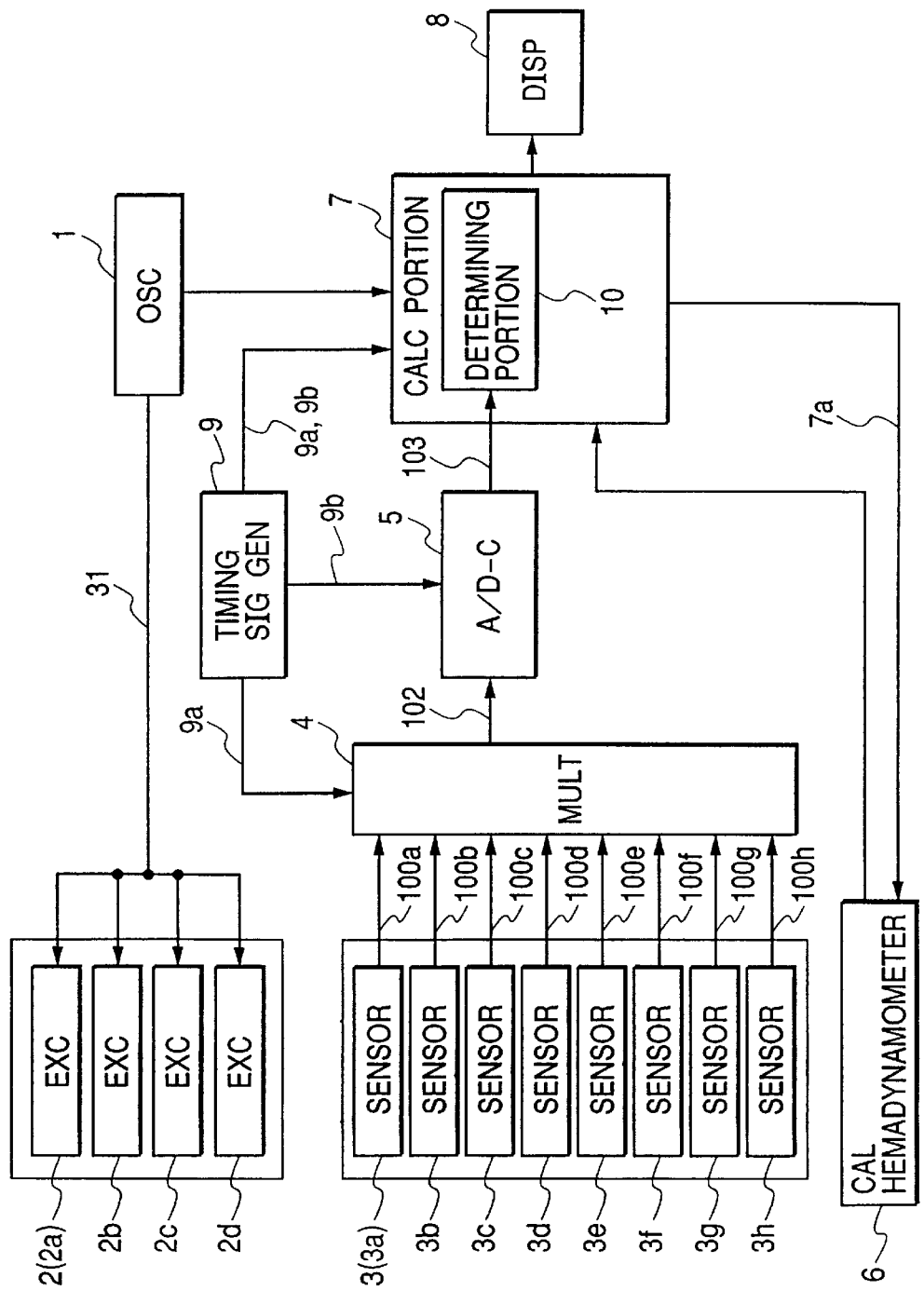
FIG. 1 is a block diagram of a noninvasive continuous blood pressure measuring apparatus of a first embodiment of this invention.
Figure 2:
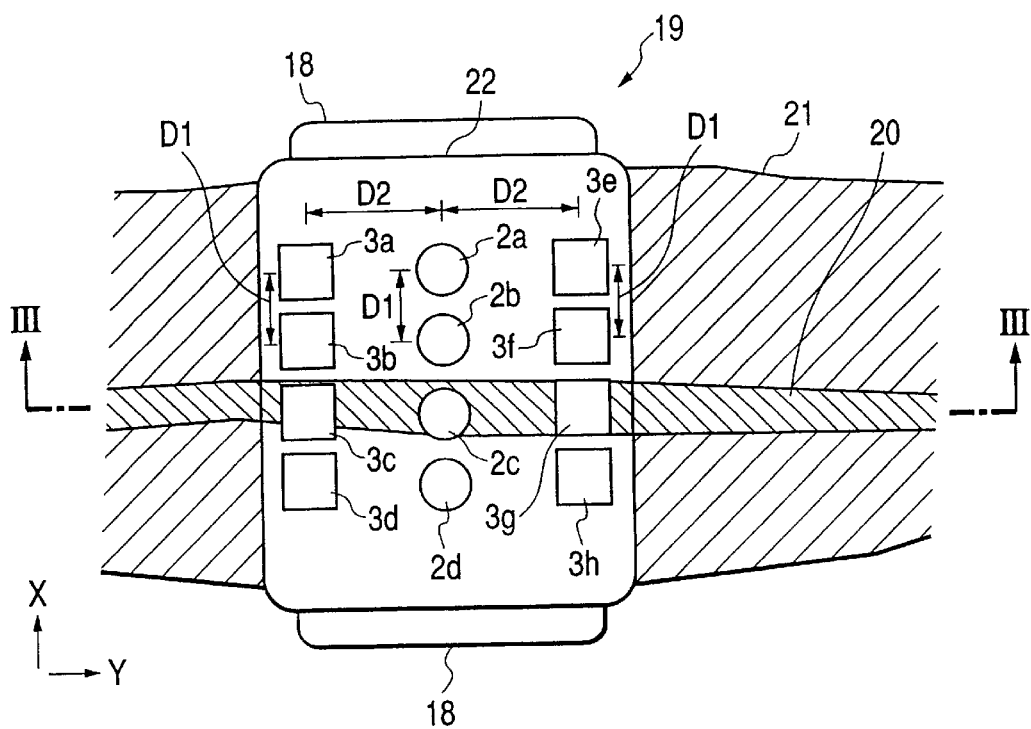
FIG. 2 is a plan view of a sensor unit of the first embodiment.
Figure 3:
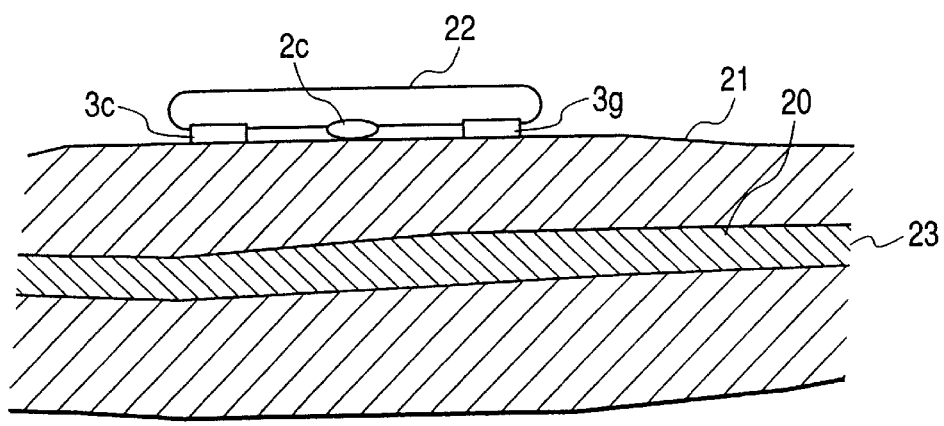
FIG. 3 is a cross-sectional side view of the sensor unit of the first embodiment taken on line III—III.

FIG. 1 is a block diagram of a noninvasive continuous blood pressure measuring apparatus of a first embodiment of this invention. FIG. 2 is a plan view of a sensor unit of the first embodiment. FIG. 3 is a side cross-sectional view of the sensor unit of the first embodiment taken on line III—III.

The noninvasive continuous blood pressure measuring apparatus of the first embodiment includes an oscillator 1 for generating an oscillation signal 31 having a predetermined (desired) frequency and a predetermined amplitude, a plurality of exciters 2 (2a to 2d) arranged in a direction X with a distance D1, responsive to the oscillation signal 31, for inducing exciter waveforms in an artery 20 and a blood 23 in the artery 20 of a living body (arm) 21, a plurality of sensors 3 (3a to 3h) arranged in the direction X with a distance D1 and apart from the column of the exciters 2 by a distance D2 respectively for receiving exciter waveforms from the living body 21 and outputting detection signals 100a to 100g, respectively, a timing signal generating circuit 9 for generating timing signals 9a and 9b, a multiplexer 4 for switching and recurrently outputting one of outputs of the sensors 3a to 3h in response to the timing signal 9a, a/d converter 5 for a/d-converting one of the outputs of the sensors 3 from the multiplexer 4, a determining portion 10 responsive to the multiplexer 4 through the a/d converter 5 for determining one of the outputs in accordance with an output of the multiplexer 4 and a predetermined judging condition such as amplitude, a calibration hemadynamometer 6 for detecting absolute-values of a maximum blood pressure and a minimum blood pressure of the living body, a calculating portion 7 for operating the calibration hemadynamometer 6 and successively calculating and outputting an instantaneous blood pressure value from a phase relation between the oscillation signal 31 and one of the outputs 100a to 100g indicated by the determination result from the determining portion 10 and the absolute values, and a display 8 for displaying a continuous blood pressure variation from the instantaneous blood pressure successively outputted by the calculation portion 7. The calibration hemadynamometer 6 may measure the absolute values of a maximum blood pressure and a minimum blood pressure of the living body periodically without controlling by the calculation portion 7. The distance D2 is constant. On the other hand, the display D1 can be varied with every sensor 3 to surely detect the exciter waveforms.

The sensor unit 19 includes a substrate 22, the exciters 2a to 2d, and sensors 3a to 3h, and an attaching belt 18 as shown in FIG. 2. The exciters 2 and the sensors 3 includes flexible plates (not shown) and piezoelectric element (not shown) sandwiched between the flexible plates, so called bimorph. The exciter 2 generates vibrations with bending in the plates generated by the piezoelectric elements. Inversely, the sensor 3 generates the detection signal from the piezoelectric element therein in accordance with the vibrations from the living body 21.

The oscillator 1 generating the oscillation signal 31 having the desired frequency and the predetermined amplitude to induce exciter a favourable waveform in the blood 23 in the artery 20. The exciters 2a to 2d respectively induce exciter waveforms in the artery 20 and the blood 23 in the artery 20 of a living body (arm) 21 in response to the oscillation signal 31. The exciter waveforms (vibrations) induced in the blood 23 transmit through the blood in the artery 20 and reach the sensors 3a to 3d. The sensors 3a to 3h receive exciter waveforms from the living body 21, i.e., the induced exciter waveforms transmitting through the artery 20 and output detection signals 100a to 100g. The timing signal generating circuit 9 generates timing signals 9a and 9b. The multiplexer 4 recurrently selecting and outputting one of detection signals 100a to 100g of the sensors 3a to 3h in response to the timing signal 9a. The a/d converter 5 a/d-converts one of the detection signals 100a to 100g of the sensor 3a to 3h. The determining portion 10 determines one of the a/d-converted detection signals in accordance with a/d-converted detection signals and a predetermined judging condition such as amplitude of the detection signals.

The calibration hemadynamometer 6 detects absolute values of a maximum blood pressure and a minimum blood pressure of the living body 21 periodically or detects the absolute values in response to a command 7a from the calculation portion 7. The calculating portion 7 operates the calibration hemadynamometer 6 and successively calculates and outputs the instantaneous blood pressure value from a phase relation between the oscillation signal 31 and one of the outputs 100a to 100g indicated by the determining result from the determining portion 10 and the absolute values. The display 8 displays the continuous blood pressure variation from the instantaneous blood pressure successively outputted by the calculation portion 7.

The determining operation will be described more specifically.

FIGS. 4A to 4E are graphical drawings of the first embodiment showing the determining operation. For convenience of explanation, it is assumed that one of the detection signals is determined between two detection signals 100c and 100d which are near the artery 20.

Figure 4A:
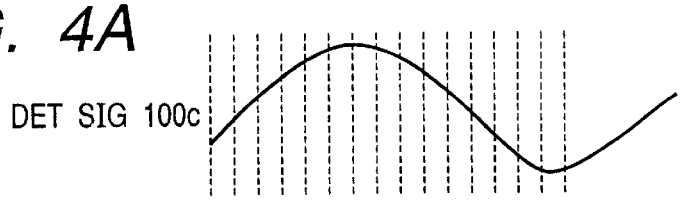
FIGS. 4A to 4E are graphical drawings of the first embodiment showing the determining operation.
Figure 4B:
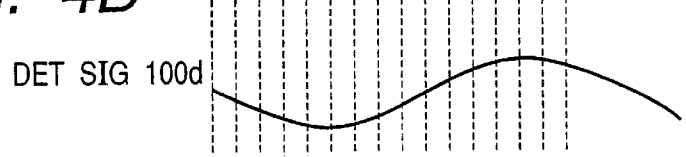

The sensors 100c and 100d outputs the detection signals as shown in FIGS. 4A and 4B, wherein an amplitude of the detection signal 100c is higher than that of the detection signal 100d because the exciter 2c and the sensor 3c are Just above the artery 20 as shown in FIG. 2.

Figure 4C:
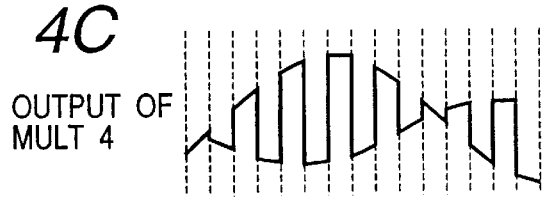

The multiplexer 4 multiplexes the detection signals 100c and 100d in response to the timing signal 9a as shown in FIG. 4C.

Figure 4D:
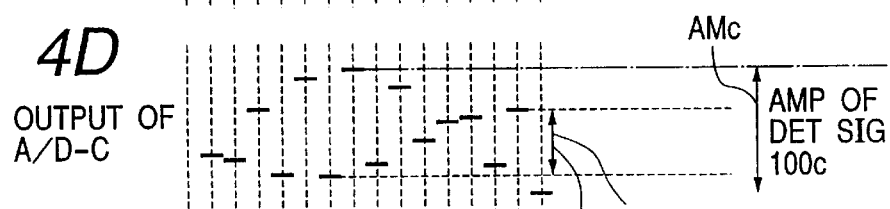
Figure 4E:
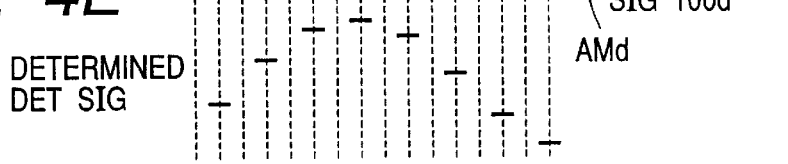

The a/d converter 4 a/d-converts the outputs of the multiplexer 4 as shown in FIG. 4D. The determining portion 10 compares the amplitude AMc of the a/d converted detection signal from the sensor 3c with the amplitude AMd of the a/d-converted detection signal 3d with reference to the timing signal 9a and determines the a/d-converted detection signal from the sensor 3c because the amplitude AMc is higher than the amplitude AMd from the sensor 3d. Then, the determining portion 10 selects and outputs a determined detection signal from the sensor 3c. In this embodiment, determining one of the a/d converted detection signal has been described with assumption that the detection signal is induced from the exciter waveform through the artery 20. However, it is also possible to determine one of the a/d-converted detection signal from the amplitude induced by the pulsation of the artery 20, that is, natural blood pressure waves. In this case, a frequency of the natural blood pressure waves is lower than the frequency of the oscillation signal 31, so that this signal is better in consideration of switching timing of the multiplexer 4 and the analog-to-digital converting rate.

In this case, a sampling frequency in the a/d converter 5 per one detection signal is equal to or more than 200 Hz. Accordingly, the resultant sampling frequency of the a/d converter 5 is equal to or more than 1600 Hz because there are eight sensor 3a to 3h.

The calculation portion 7 calculates and outputs the instantaneous blood pressure value from a phase relation between the oscillation signal 31 and one of the detection signals 100a to 100g indicated by the determining result from the determining portion 10 and the absolute values. That is, the method of calculating the blood pressure from the sound velocity through artery is known and described in U.S. Pat. No. 5,590,649, the disclosure of which is hereby incorporated by reference.

In FIG. 2, the substrate 22 correspondingly arranges the exciter units 2a to 2d and the sensors 3a to 3h such that each pair (for example, 2a, 3a, and 3e) includes two of the sensors 3 and one of the exciters 2 arranged between two of the sensors with the distance D2 and is arranged in the direction X, so that it is easy to attach the substrate 22 with the attaching belt 18 because accurate positioning with respect to the artery 20 can be omitted by the selecting operation of the detection signals. In FIG. 2, the detection signal 100g may be selected by determining portion 10 in accordance with the amplitudes of the detection signals 100c and 100g. Moreover, it is possible to select the sensor 3 positioned upstream of the artery 20 or positioned downstream with respect to the exciter 2 at will with a request receiving portion (not shown).

(SECOND EMBODIMENT)

Figure 5A:
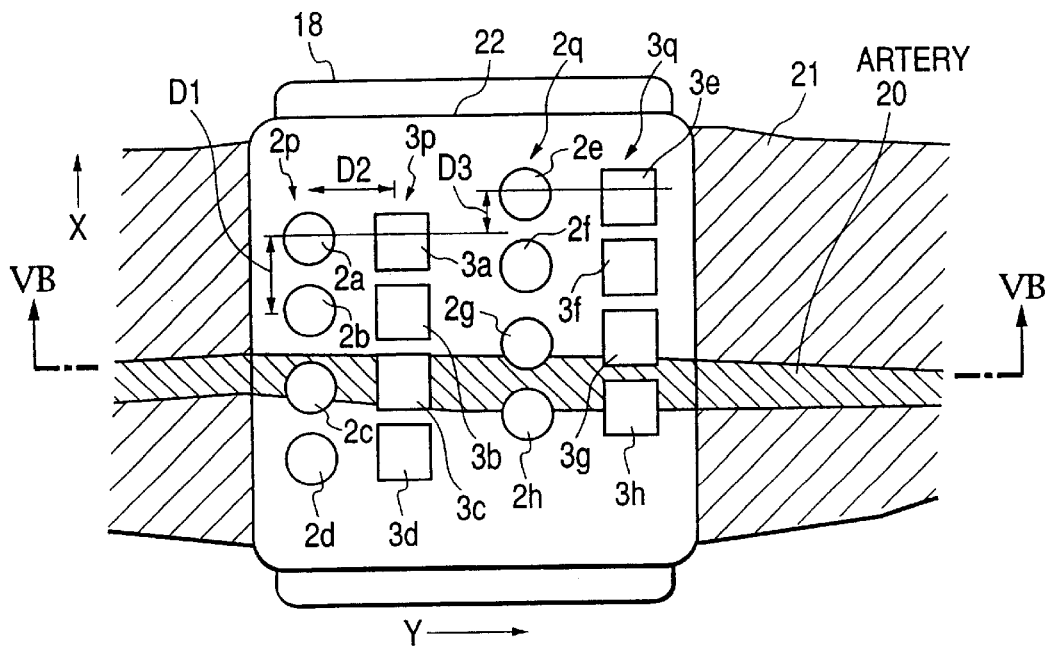
FIG. 5A is a plan view of a sensor unit of a second embodiment.
Figure 5B:
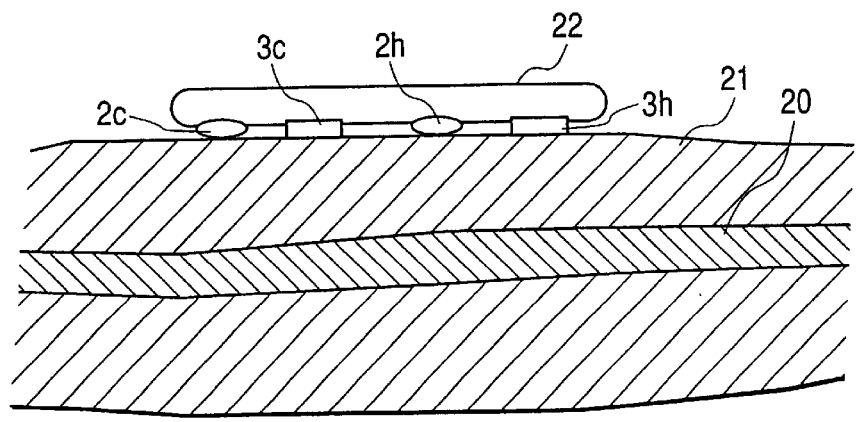
FIG. 5B is a cross-sectional side view of the sensor unit of the second embodiment taken on the line VB in FIG. 5A.

FIG. 5A is a plan view of a sensor unit of a second embodiment. FIG. 5B is a cross-sectional side view of the sensor unit of the second embodiment taken on the line VB in FIG. 5A.

The sensor unit of the second embodiment includes a substrate 22, exciters 2a to 2h, sensors 3a to 3h, and an attaching belt 18. A column 2q of the exciters 2e to 2h and corresponding column 3q of the sensors 3e to 3h are shifted in the direction X from the column 2p of the exciters 2a to 2d and the column 3p of the sensors 3a to 3d by a distance D3 which is a half of the distance (pitch) D1. The exciters 2a to 2d and the sensors 3a to 3d are arranged with the distance D1 in direction X which substantially corresponds to the size of the exciters 2a to 2d and the sensors 3a to 3d in the direction X. Therefore, the exciters 2a to 2d and the sensors 3a to 3d are arranged compactly and selecting one of the detection signals are precisely effected.

(THIRD EMBODIMENT)

Figure 6:
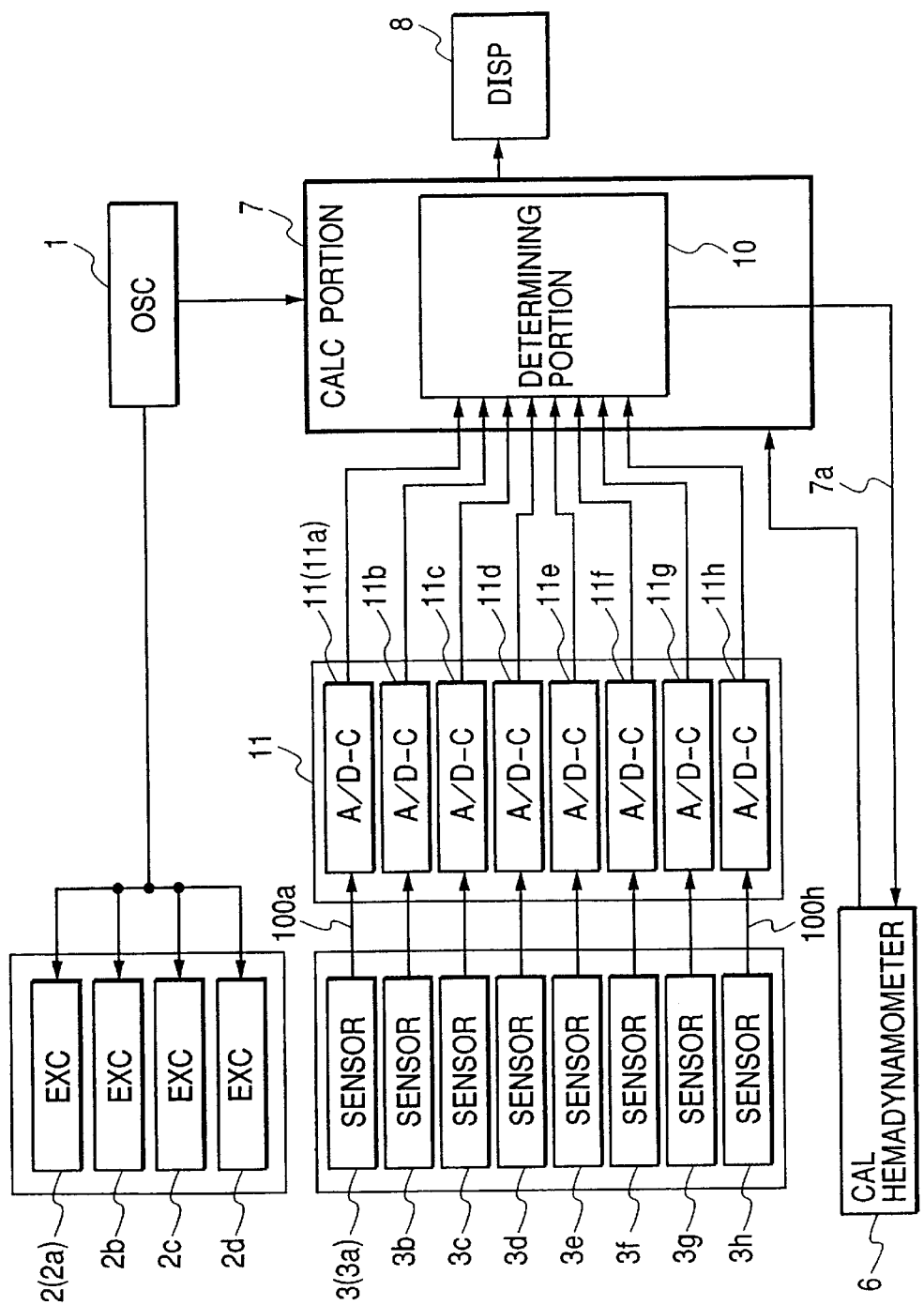
FIG. 6 is a block diagram of a noninvasive continuous blood pressure measuring apparatus of a third embodiment of this invention.

FIG. 6 is a block diagram of a noninvasive continuous blood pressure measuring apparatus of a third embodiment of this invention. The noninvasive continuous blood pressure measuring apparatus of the third embodiment is substantially the same as that of the first embodiment. The difference is that a/d converters 11a to 11h are respectively provided to the detection signals 100a to 100h instead the multiplxer 4 and the a/d converter 5. The a/d converters 11a to 11h a/d-converts the detection signals 100a to 100h independently. The determining portion 10 selects and outputs a determined detection signal from the sensor 3.

The calculating portion 7 operates the calibration hemadynamometer 6 and successively calculates and outputs the instantaneous blood pressure value from a phase relation between the oscillation signal and one of the outputs 100a to 100g from the determining portion 10 and the absolute values. The display 8 displays the continuous blood pressure variation from the instantaneous blood pressure successively outputted by the calculation portion 7.

In the third embodiment, a total sampling rate of the a/d converters 11a to 11h is increased, so that an accuracy in measuring the continuous blood pressure variation is improved.

(FOURTH EMBODIMENT)

Figure 7:
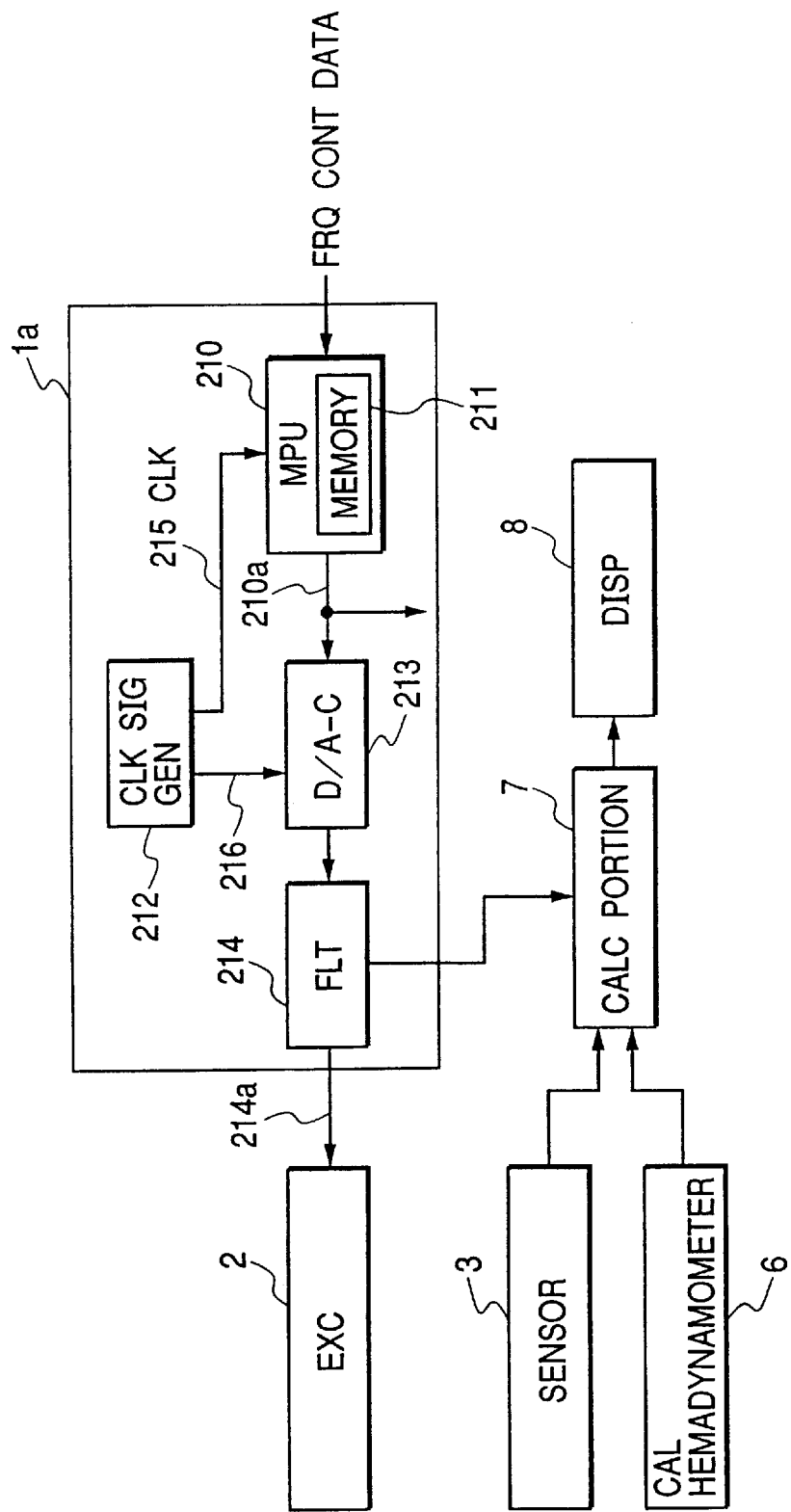
FIG. 7 is a block diagram of a noninvasive continuous blood pressure measuring apparatus of a fourth embodiment of this invention.

FIG. 7 is a block diagram of a noninvasive continuous blood pressure measuring apparatus of a fourth embodiment of this invention. The noninvasive continuous blood pressure measuring apparatus of the fourth embodiment is substantially the same as that of the first embodiment. The difference is that a frequency of the oscillator 1a is controlled.

The oscillator 1a includes a clock signal generation circuit 212 for generating a clock signal; a microprocessor 210, including a memory 211, responsive to frequency control data and the clock signal for successively generating frequency signal data 210a indicative of amplitude in time base in accordance with the frequency control data; a d/a converter 213 for converting the frequency signal data, and outputting a frequency signal; and a filter 214 for low-pass-filtering the frequency signal and outputting the filtered frequency signal as the oscillation signal of which frequency controlled in accordance with the frequency data.

Figure 8:
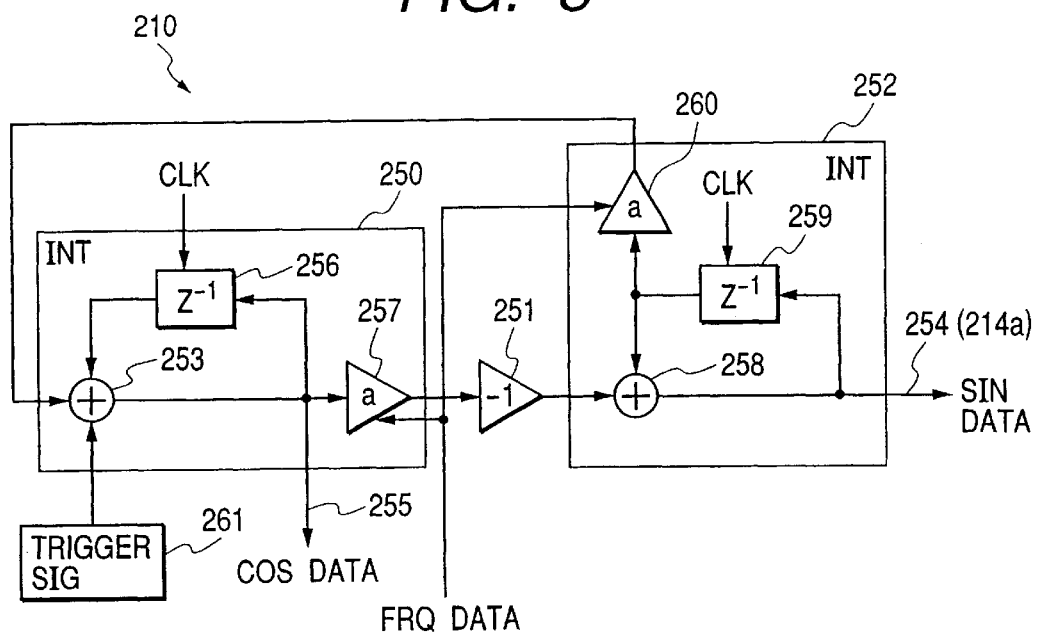
FIG. 8 is a block diagram of the fourth embodiment, wherein the operation of the microprocessor is equivalently shown.

FIG. 8 is a block diagram of the fourth embodiment, wherein the operation of the microprocessor 210 is equivalently shown.

The clock signal generation circuit 212 generates the clock signal 215 and a conversion timing signal for the a/d converter 213. The microprocessor 210 starts an operation for calculating frequency signal data 210a indicative of amplitude in response to every clock signal 215 from the clock signal generation circuit 212 using the memory 211 as a work memory by the known double integration method. The a/d converter 213 converts the frequency signal data to generate the oscillation signal. The filter 214 filters the oscillation signal from the a/d converter 213 to remove unnecessary frequency components to supply the oscillation signal 214a with low spurious.

The calculation portion 7 may be provided by the same microprocessor 210.

FIG. 8 shows a circuit which is equivalent to the operation of the microprocessor 210.

The circuit for effecting the double integration method includes first integrator 250, an inverter for inverting an output of the integrator 250, and a second integrator 252 for integrating an output of the inverter 251 and outputting sine data 254 and feed back data which is supplied to the first integrator 250.

The first integrator 250 includes an adder 253, a multiplier 257, a delay 256. The adder 253 sums the feedback data from a multiplier 260 in the second integrator 252, an output of the delay 256 and a trigger signal 261 which is generated once at start of the operation of the oscillator 1a. The summing result is supplied to the delay 256 and to the multiplier 257 and outputted as a cosine data 255. The multiplier 257 multiplies the cosine data 255 with frequency data "a". The delay 256 supplied with the clock signal 215 delays the summing result of the adder 253 by one clock period of the clock signal 215.

The inverter 251 having a gain of −1 and inverts the multiplying result.

The second integrator 252 includes an adder 258, a multiplier 260, and a delay 259. The adder 258 sums an output of the delay 259 and an output of the inverter 251 The summing result of the adder 258 is supplied to the delay 259 and outputted as a sine data 254. The delay 259 supplied with the clock signal 215 delays the summing result of the adder 258 by one clock period of the clock signal 215. The output of the delay 259 is supplied to the multiplier 260 which multiplies the output of the delay 259 with the frequency data "a" and supplies the feedback data to the adder 253 as mentioned. The delay 256 and 259 are supplied with the clock signal 215 to delay the cos data 255 and the sin data 254 by one clock signal interval.

This circuit generates the oscillation signal 214a of which frequency f is given by:

$$f=(a \times T)/(2 \times \pi)$$

where T is a frequency of the clock signal 215 generated by the clock signal generation circuit 212.

As mentioned, the circuit generates the oscillation signal 214a of which frequency f is controlled by the frequency control data "a". Moreover, as the oscillation signal, the sine data 254 and the cosine data 255 are generated and are also supplied to the calculation portion 7 at the same time.

(FIFTH EMBODIMENT)

Figure 9:
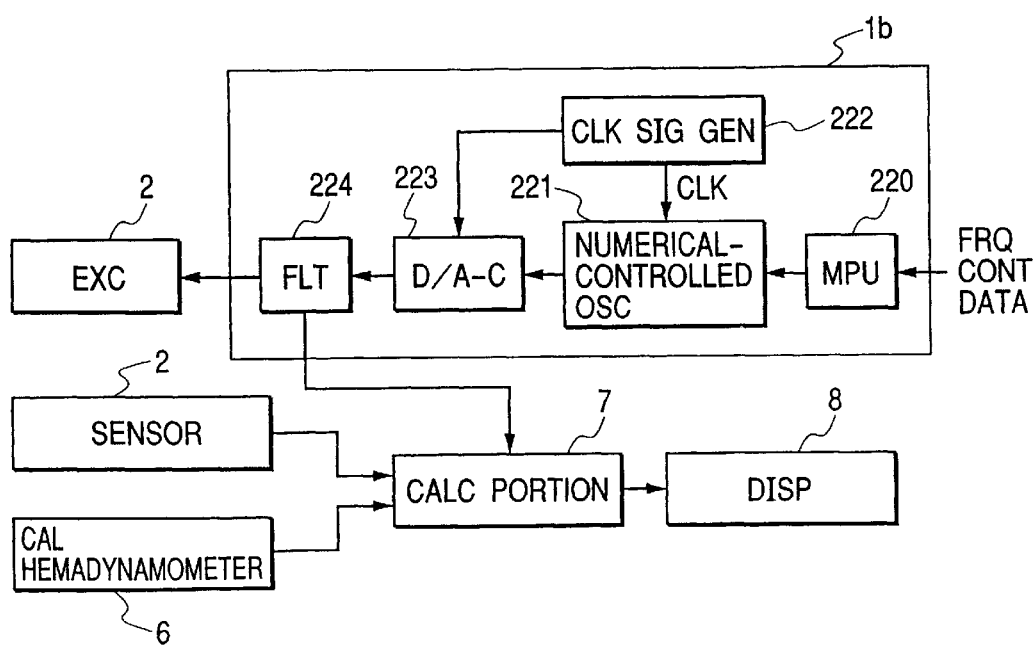
FIG. 9 is a block diagram of a noninvasive continuous blood pressure measuring apparatus of a fifth embodiment of this invention.

FIG. 9 is a block diagram of a noninvasive continuous blood pressure measuring apparatus of a fifth embodiment of this invention. The noninvasive continuous blood pressure measuring apparatus of the fifth embodiment is substantially the same as that of the fourth embodiment. The difference is in the structure of the oscillator 1b. The oscillator 1b includes a clock signal generation circuit 222 for generating a clock signal; a microprocessor 220 for receiving frequency control data; a numerically controlled oscillator 221 for successively generating frequency control data indicative of amplitude in time base in accordance with the frequency control data; a d/a converter 223 for converting the frequency signal data, and outputting a frequency signal; and a filter 224 for low-pass-filtering the frequency signal and outputting the filtered frequency signal as the oscillation signal of which frequency controlled in accordance with the frequency data "a".

The microprocessor 220 receives the frequency control data. The numerically-controlled oscillator 221 successively generates the frequency control data in accordance with the frequency control data. The d/a converter 223 converts the frequency signal data and outputs a frequency signal. The filter 224 low-pass-filters the frequency signal and outputting the filtered frequency signal as the oscillation signal of which frequency controlled in accordance with the frequency data (SIXTH EMBODIMENT)

Figure 10:
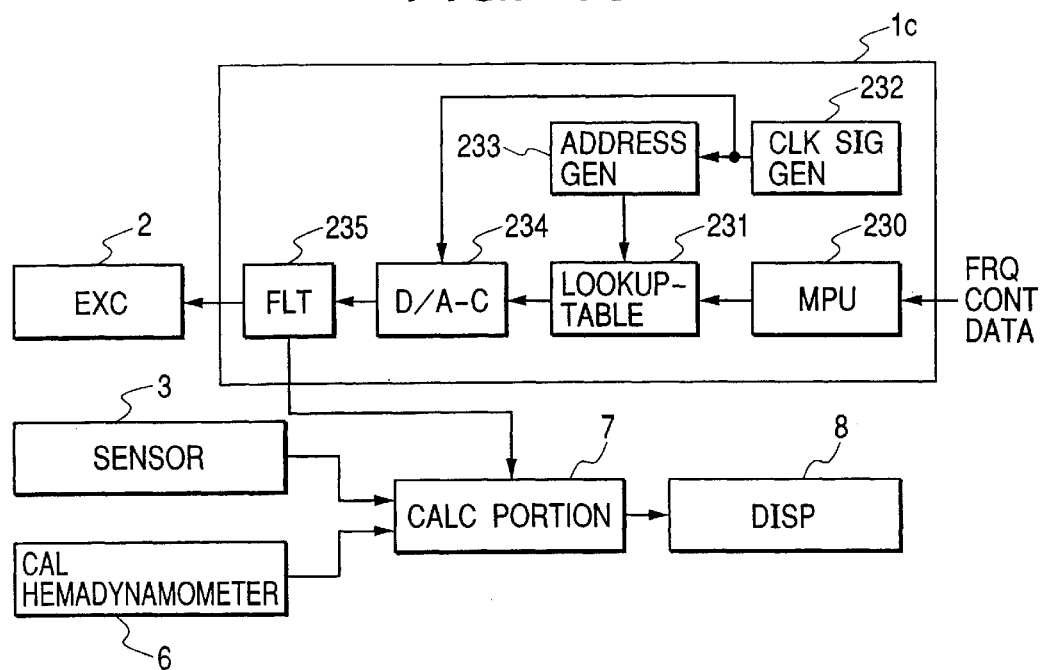
FIG. 10 is a block diagram of a noninvasive continuous blood pressure measuring apparatus of a sixth embodiment of this invention.

FIG. 10 is a block diagram of a noninvasive continuous blood pressure measuring apparatus of a sixth embodiment of this invention. The noninvasive continuous blood pressure measuring apparatus of the sixth embodiment is substantially the same as that of the fourth embodiment. The difference is in the structure of the oscillator 1c. The oscillator 1c includes a clock signal generation circuit 232 for generating a clock signal; a look-up table 231; a microprocessor 230 for receiving frequency control data and generating a set of frequency signal data indicative of amplitude for one cycle of the oscillation signal in accordance with the frequency control data and storing the frequency signal data in a look-up table 231; an address signal generation circuit 233 for successively generating an address signal in response to the clock signal to operate the look-up table 231 to successively output instantaneous frequency signal data; a d/a converter 234 for a/d-converting the frequency signal data and outputting a frequency signal; and a filter 235 for low-pass-filtering the frequency signal and outputting the filtered frequency signal as the oscillation signal of which frequency controlled in accordance with the frequency data "a".

The microprocessor 220 receives the frequency control data and generates the set of frequency signal data indicative of amplitude for one cycle of the oscillation signal in accordance with the frequency control data and stores the frequency signal data in the look-up table 231 before the start of measuring the blood pressure. The address signal generation circuit 233 successively generates the address signal in response to the clock signal to operate the look-up table 231 to successively output the instantaneous frequency signal data. The d/a converter 234 d/d-converts the frequency signal data and outputs the frequency signal. The filter 235 low-pass-filters the frequency signal and outputs the filtered frequency signal as the oscillation signal of which frequency controlled in accordance with the frequency data "a".

(SEVENTH EMBODIMENT)

Figure 11:
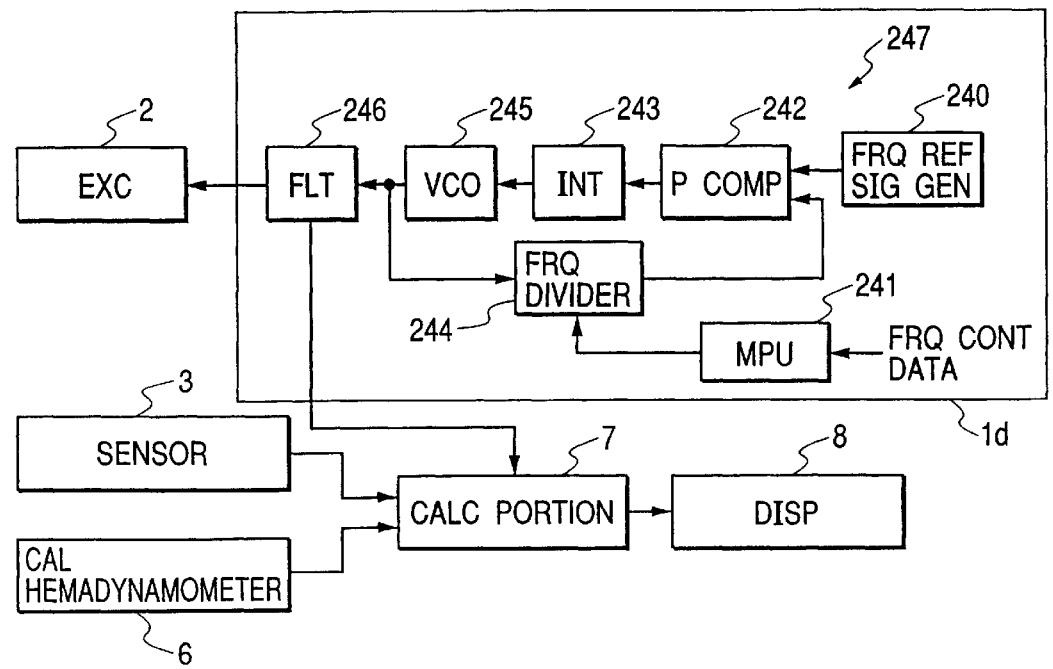
FIG. 11 is a block diagram of a noninvasive continuous blood pressure measuring apparatus of a seventh embodiment of this invention.

FIG. 11 is a block diagram of a noninvasive continuous blood pressure measuring apparatus of a seventh embodiment of this invention. The noninvasive continuous blood pressure measuring apparatus of the seventh embodiment is substantially the same as that of the fourth embodiment. The difference is in the structure of the oscillator. The oscillator 1d of the seventh embodiment includes a microprocessor (MPU) 241 for receiving frequency control data, a PLL circuit 247, and a filter 246. The PLL circuit 247 includes a frequency reference signal generating circuit 240 for generating a frequency reference signal, a phase comparator 242 for detecting a phase difference between the frequency reference signal generating circuit 240 and a frequency-divided signal, an integrator 243 for integrating an output of the phase comparator 242, a voltage-controlled oscillator 245 for generating an oscillation signal of which frequency controlled in accordance with the output of the integrator, i.e., the integrated phase difference, and a frequency divider 244 for frequency-dividing the oscillation signal from the voltage controlled-oscillator 245 by the frequency control data from the microprocessor 241. The filter 246 removes unnecessary components in the oscillation signal from the voltage controlled oscillator 245 and supplies the filtered oscillation signal to the exciter 2 and the calculation portion 7. The frequency of the oscillation signal and the vibration frequency of the exciter 2 are controlled in accordance with the frequency control data.

(EIGHTH EMBODIMENT)

Figure 12:
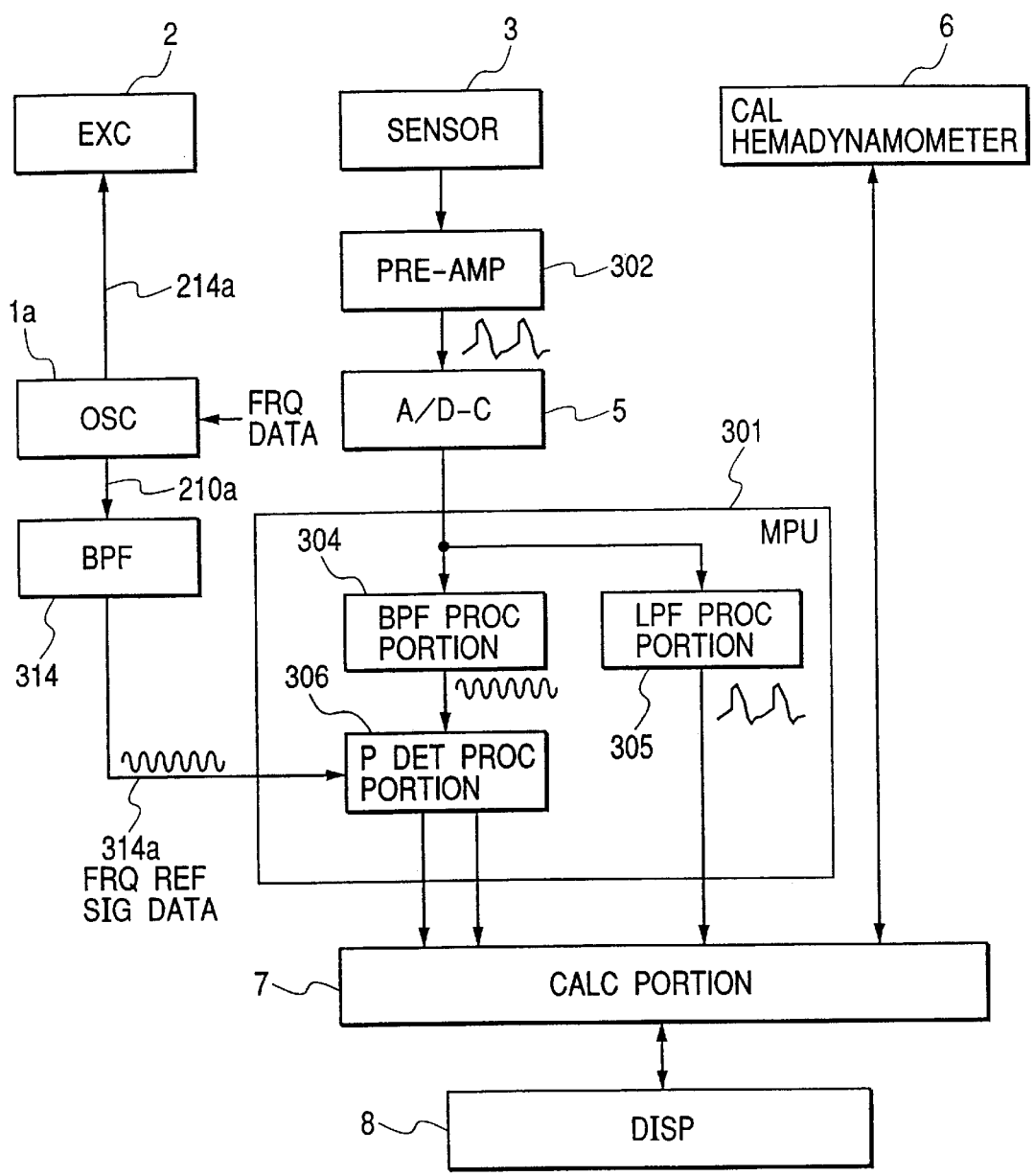
FIG. 12 is a block diagram of a noninvasive continuous blood pressure measuring apparatus of an eighth embodiment of this invention.

FIG. 12 is a block diagram of a noninvasive continuous blood pressure measuring apparatus of an eighth embodiment of this invention. The noninvasive continuous blood pressure measuring apparatus of the eighth embodiment is substantially the same as that of the fourth embodiment. The difference is that a microprocessor 301 is further provided for filtering processes and a phase detection process.

The noninvasive continuous blood pressure measuring apparatus of the eighth embodiment includes the oscillator 1a for generating the oscillation signal 214a of which frequency controlled to a predetermined (desired) frequency and the corresponding oscillation signal data 210a, a bandpass filter 314 for bandpass-filtering the oscillation signal data 210a and outputting frequency reference signal data 314a, the exciter 2 for inducing exciter waveforms in an artery 20 and-a blood 23 in the artery of a living body (arm) 21, the sensor 3 apart from the exciter 2 by a distance D2 for receiving exciter waveforms and a natural blood pressure waveform from the living body and outputting a detection, signal, a pre-amplifier 302 for amplifying the detection signal including a plurality of patient's physiological parameters, an a/d converter S for a/d-converting an output of the pit-amplifier 302 to output detection data, the microprocessor 301 for effecting a bandpass filtering process for detecting the exciter waveform and a low pass filtering process for detecting a natural blood pressure wave form from the detection data and a phase detection process to output phase difference data, a calibration hemadynamometer 6 for detecting absolute values of a maximum blood pressure and a minimum blood pressure of the living body, a calculating portion 7 for successively calculating and outputting an instantaneous blood pressure value from a phase relation between the frequency reference signal data and the detected exciter waveform and the detected natural blood pressure waveform and the absolute values from the calibration hemadynamometer 6, and a display 8 for displaying a continuous blood pressure variation from the instantaneous blood pressure successively outputted by the calculation portion 7.

The bandpass filtering process portion 304 in the microprocessor 301 detects the exciter waveform from the detection data and the low pass filtering process portion 305 detects the natural blood pressure waveform from the detection data. The phase detection process portion 305 detects a phase difference between the frequency reference signal data 314a and the detected exciter waveform from the bandpass processing portion 304 and outputs the phase difference data including a real number component of the phase shift and an imaginarily number component of the phase shift.

The calculating portion 7 successively calculates and outputs an instantaneous blood pressure value from the phase difference data, the detected natural blood pressure waveform, and the absolute values from the calibration hemadynamometer 6. The display 8 displays a continuous blood pressure variation from the instantaneous blood pressure successively outputted by the calculation portion 7.

Figure 13A:
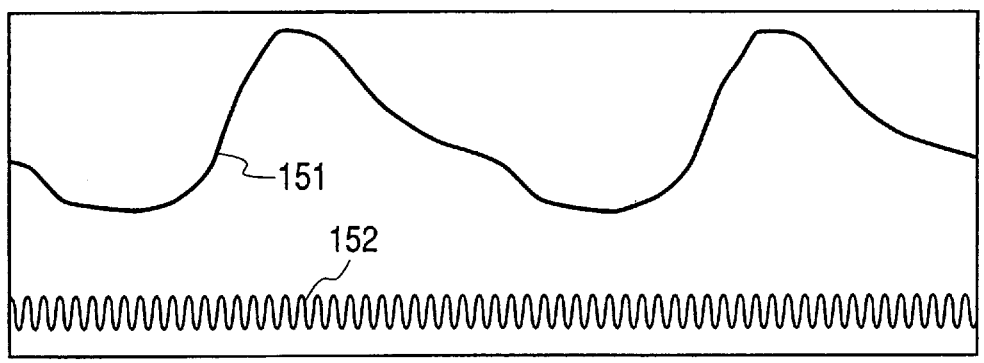
FIGS. 13A and 13B are graphical drawing of the eighth embodiment.
Figure 13B:
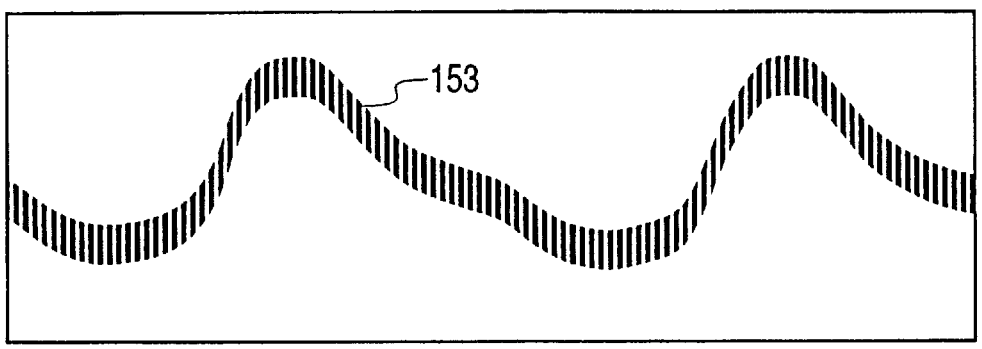

FIGS. 13A and 13B are graphical drawing of the eighth embodiment. The sensor receives the vibrations from the living body including the exciter waveform and the natural blood pressure waveform superimposed with each other. The bandpass filtering processing portion 304 extracts the exciter waveform 152 and the low pass filter processing portion 305 extracts the natural blood pressure waveform 151.

The band pass filter 314 may be omitted if the oscillation signal data 210a includes unnecessary components. The microprocessor 301 may also effect the processing in the calculation portion 7.

(NINTH EMBODIMENT)

Figure 14:
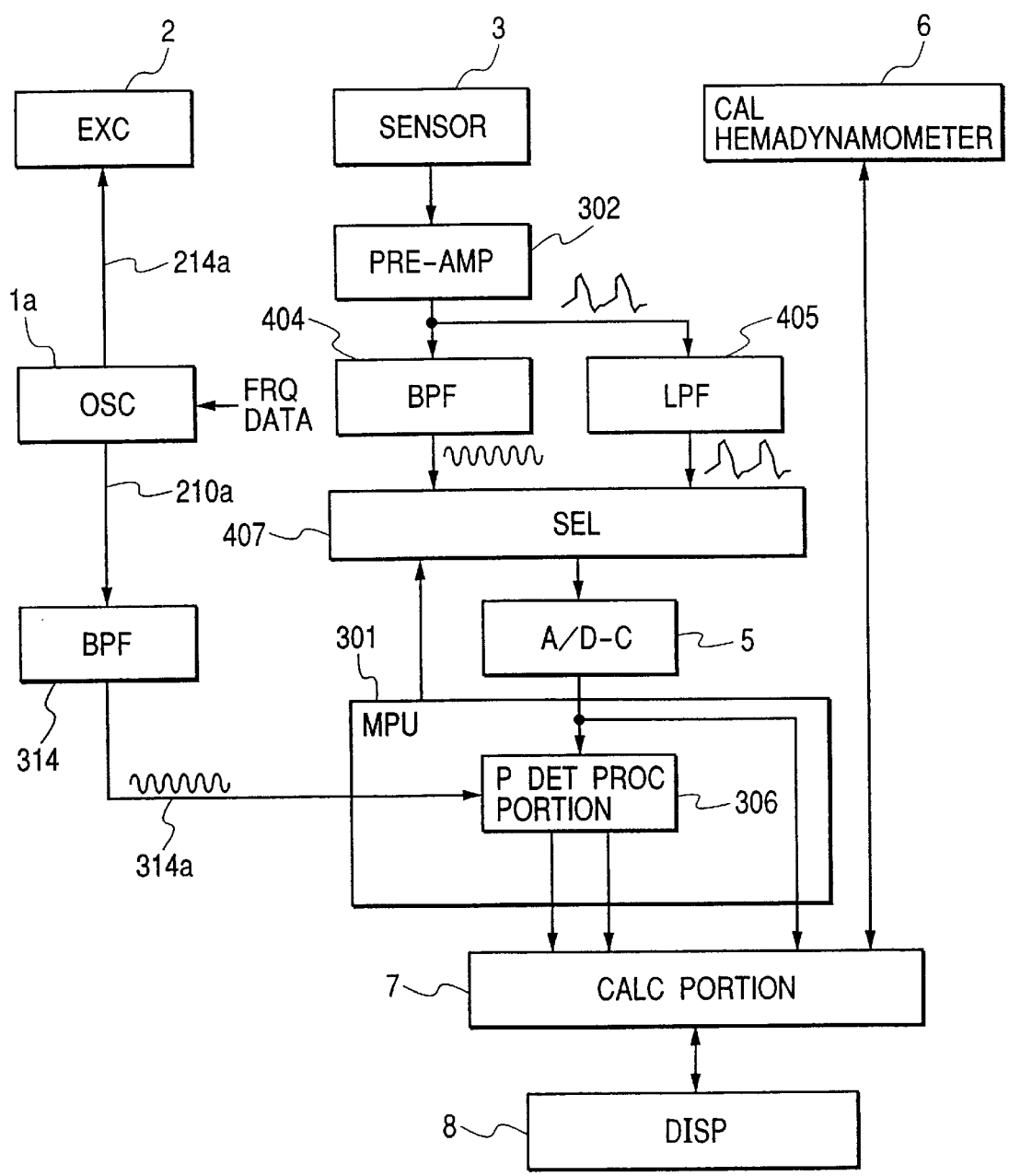
FIG. 14 is a block diagram of a noninvasive continuous blood pressure measuring apparatus of a ninth embodiment of this invention.

FIG. 14 is a block diagram of a noninvasive continuous blood pressure measuring apparatus of a ninth embodiment of this invention. The noninvasive continuous blood pressure measuring apparatus of the ninth embodiment is substantially the same as that of the ninth embodiment. The difference is that the bandpass filtering process is effected by a bandpass filter 404 instead the bandpass filtering processing portion 304, the low pass filtering processing is effected by a low pass filter 405 instead the low pass filtering processing portion 305, a selector 407 is further provided to supplying either of an output of the bandpass filter 404 and an output of the low pass filter 405 to the a/d converter 5.

The sensor 3 receives the induced exciter waveform and natural blood pressure waveform from the living body and outputting detection signal. The pre-amplifier 302 amplifies the detection signal including a plurality of patient's physiological parameters. The bandpass filter 404 extracts the exciter waveform. The low pass filter 405 extracts the natural blood pressure waveform. The selector switchably outputs either of the exciter waveform from the bandpass filter 404 or the natural blood waveform from the low pass filter 405 in response to a switching control signal from the microprocessor 301. The a/d converter 5 a/d-converts the exciter waveform and the natural blood pressure waveform. The phase detection process portion 306 detects the phase difference between the frequency reference signal data 314a and an output of the a/d converter 5 while the selector selects the exciter waveform and outputs the phase difference data. The calculating portion 7 successively calculates and outputs an instantaneous blood pressure value from the phase difference data from the phase detection processing portion 306, the natural blood pressure wave form from the a/d converter 5 while the selector 407 selects the natural blood pressure wave form, and the absolute values from the calibration hemadynamometer 6. The display 8 displays a continuous blood pressure variation from the instantaneous blood pressure successively outputted by the calculation portion 7.

(TENTH EMBODIMENT)

Figure 15:
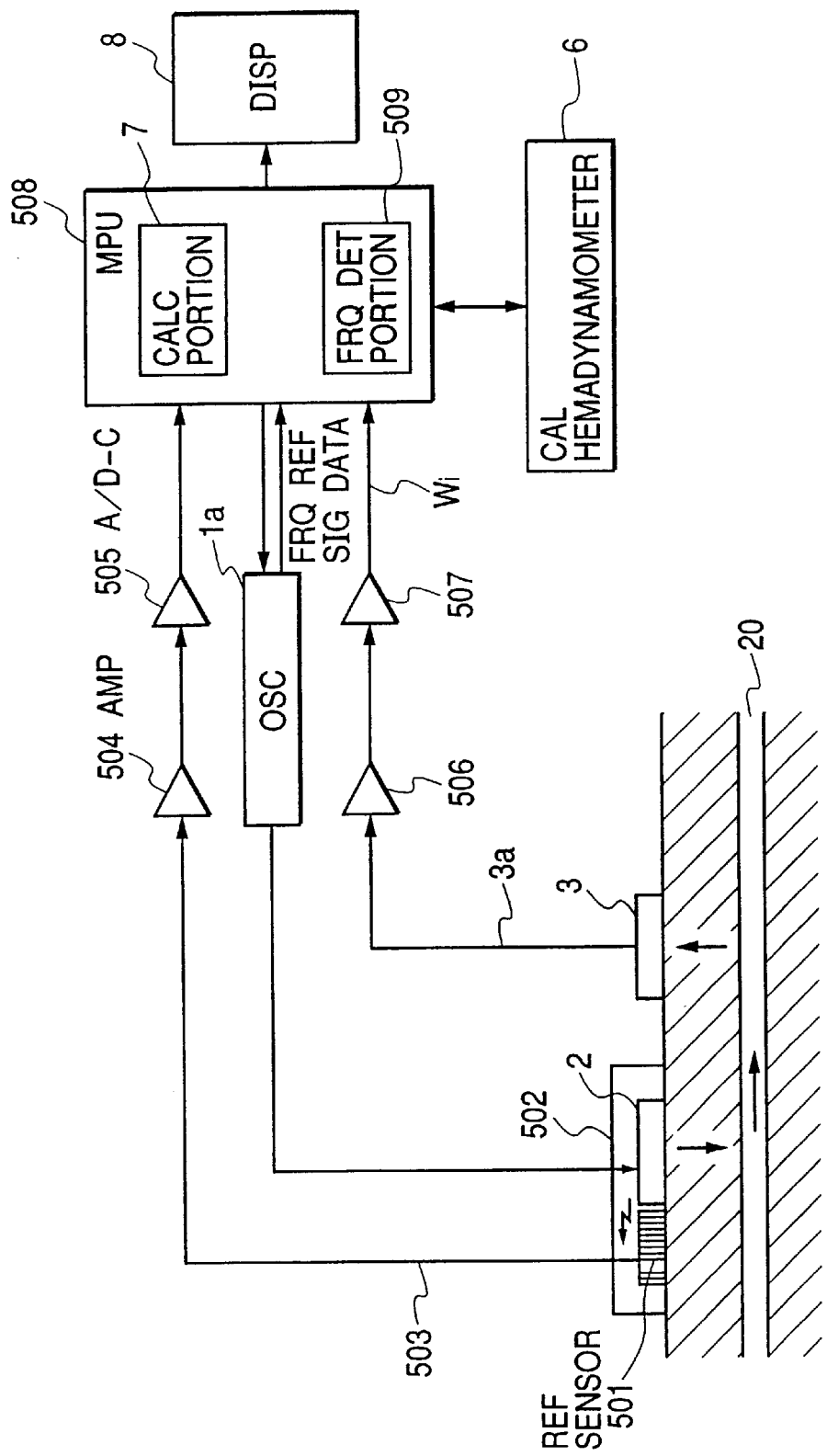
FIG. 15 is a block diagram of a noninvasive continuous blood pressure measuring apparatus of a tenth embodiment of this invention.

FIG. 15 is a block diagram of a noninvasive continuous blood pressure measuring apparatus of a tenth embodiment of this invention. The noninvasive continuous blood pressure measuring apparatus of the tenth embodiment is substantially the same as that of the fourth embodiment. The difference is that a reference sensor 501 is further provided with the exciter 2, an amplifier 504 for amplifying the reference sensor detection signal from the reference sensor 501, and a a/d converter 505 for a/d-converting the sensor detection signal from the amplifier 504, and a frequency determining portion 509 are further provided. The reference sensor 501 detects the vibrations from the exciter 2. A substrate 502 supports the exciter 2 and the reference sensor 501.

Figure 16:
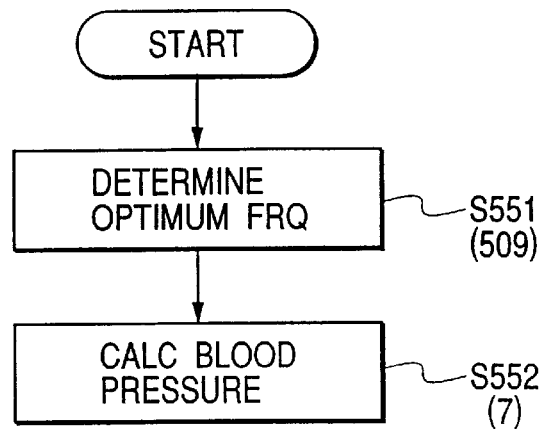
FIG. 16 depicts a flow chart of the tenth embodiment showing an operation of the microprocessor.

FIG. 16 depicts a flow chart of the tenth embodiment showing an operation of the microprocessor 508.

Before detecting the continuous blood pressure, the frequency determining portion 509 successively generates and supplies frequency control data indicative of a frequency fi (f1 to fn) to the oscillator 1a for T seconds and successively detects the detection signal from the sensor 3 and the reference sensor detection signal 503 for the interval of T seconds to determine the optimum frequency and supplies the frequency control data indicative of the optimum frequency in step S551. When the optimum frequency has been determined, the microprocessor 508 successively calculates the instantaneous blood pressure in step S552 at the optimum frequency, so that the display 8 displays the continuous blood pressure variation from the successively supplied blood pressure from the calculation portion 7.

Figure 17:
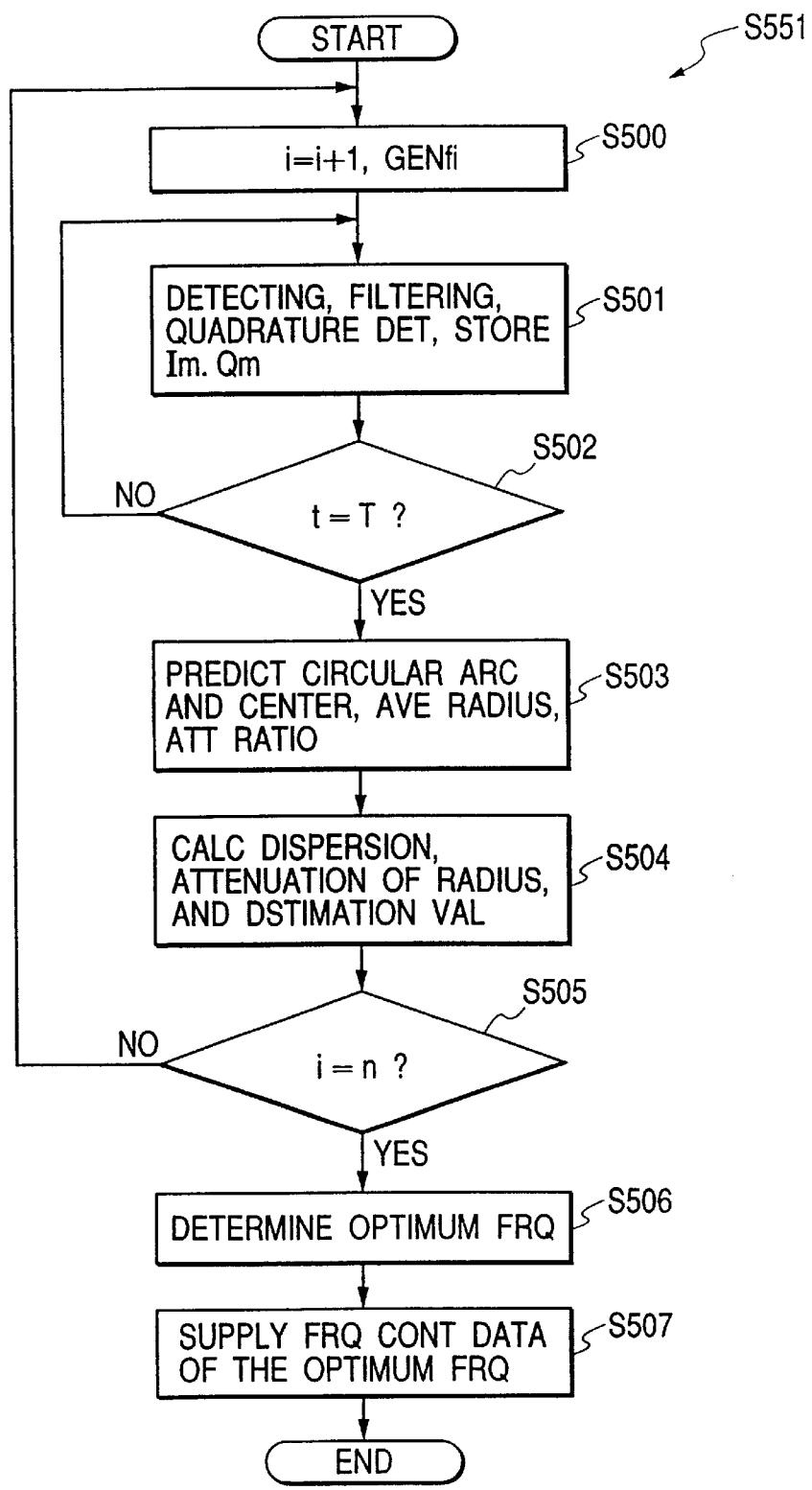
FIG. 17 depicts a flow chart of the tenth embodiment showing an operation of the frequency determining portion.

FIG. 17 depicts a flow chart of the tenth embodiment showing an operation of the frequency determining portion 509, that is, the step S551.

At first, the frequency determining portion 509 generates the frequency control data indicative of a frequency f1 for the interval of T seconds in step S500. During the interval of T seconds, the oscillator 1a generates the oscillation signal having a frequency f1, i.e., A sin (2πf1t). The exciter 2 generates vibration of the frequency f1, so that the exciter waveform is induced in the artery 20.

In the following step S501, the reference sensor 501 detects the vibrations of the exciter 2 and generates the reference sensor detection signal 503 which is supplied to the microprocessor 508 through the amplifier 504 and the a/d converter 505 at the oscillation frequency f1. The sensor 3 detects the exciter waveform transmitted through the artery 20 and generates the detection signal 3a which is supplied to the microprocessor 508 through the amplifier 506 and the a/d converter 507 at the oscillation frequency f1. Further, the frequency determining portion 509 extracts the frequency component f1 from the detection signal from the sensor 3 and extracts the frequency component f1 of the reference sensor detection signal by a filtering process.

Moreover, the frequency determining portion 509 effects a quadrature detection to obtain and store a real number component (I component) and an imaginarily number component (Q component) of the phase shift between the frequency reference signal data and the detection signal from the sensor 3. The processing in step S501 is repeated for T seconds.

Figure 18:
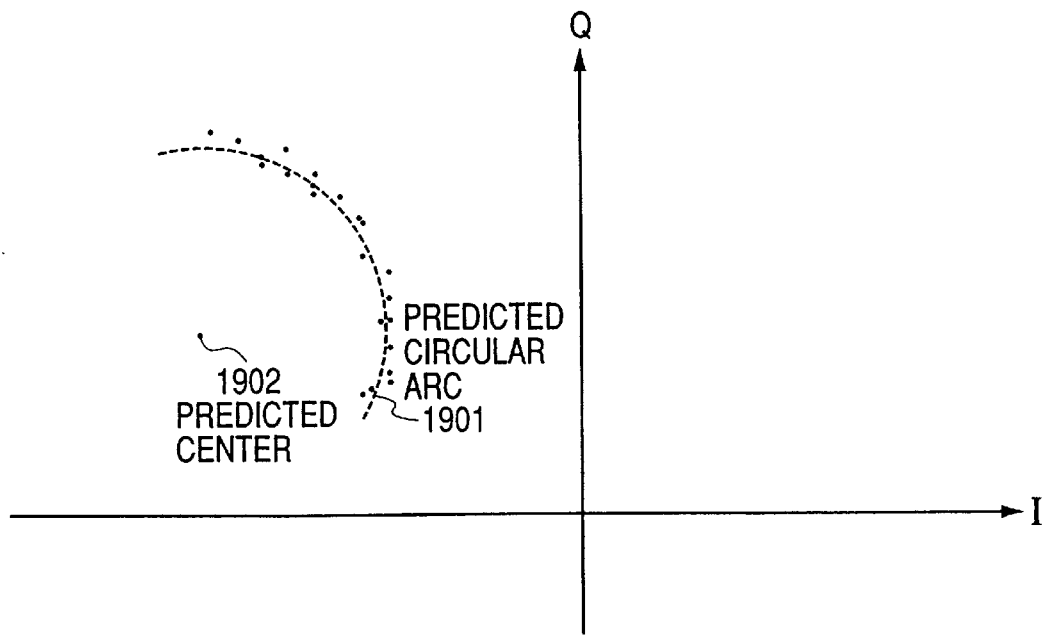
FIG. 18 is a graphical drawing of the tenth embodiment.

FIG. 18 is a graphical drawing of the tenth embodiment.

When t=T (sec) in step S502, the frequency determining portion 509, in step S503, predicts a circular arc 1901 of the I and Q components ((I1, Q1),(I2, Q2), . . . ,(Im, Qm)) of the phase shift at the frequency f1 in an I-Q plane as shown in FIG. 18 and predicts a center 1902 of the circular arc 1901 and obtains distances, i.e., radiuses, (r1, r2, . . . , rm) between the respective points (I1, Q1),(I2, Q2), . . . ,(Im, Qm) and the predicted center 1902 of the circular arc 1901 (m is a natural number more than one) and calculates an average radius Rf1AVe and attenuation ratio Pf1 with respect to the amplitude Aex of the reference sensor detection signal from the reference sensor 501 as follows:

$$Pf1 = 1 \cdot (Rf1Ave/Aex)$$

The frequency determining portion 509, in step S504 calculates a dispersion value Rf1Var of the radiuses r1, r2, . . . , rm. Moreover, optimum frequency estimation value Zfi is obtained:

$$Zf1 = \alpha \cdot (Pf1/PStd) + \beta \cdot (Rf1Var/RStd)$$

Then, processing returns to step S500 to generates the oscillation signal having a frequency f2.

The processing from steps S500 to S505 is repeated until i=n (n is a natural number).

Then, the optimum frequency estimation values of f1 to fn are obtained from the equation:

$$Zfi = \alpha \cdot (Pfi/PStd) + \beta \cdot (RfiVar/RStd)$$

Then, in step S506, the optimum frequency showing the lowest the optimum frequency estimation value is selected. In the following step S507, the frequency determining portion 509 supplies the frequency control data of the optimum frequency.

In the equation for obtaining the optimum frequency estimation value, $\alpha$ and $\beta$ are weighting coefficients which are determined in accordance with degrees of importance of the estimation element of (Pfi/PStd) and (RfiVar/RStd).

In this embodiment, the reference sensor 501 is used. However, this sensor can be omitted because the amplitude of the vibrations of the exciter 2 is substantially constant over a necessary frequency range. Moreover, it is possible that the amplitudes of the reference sensor detection signal with respect to f1 to fn can be measured and stored in advance to be used in step S501.

(ELEVENTH EMBODIMENT)

Figure 19:
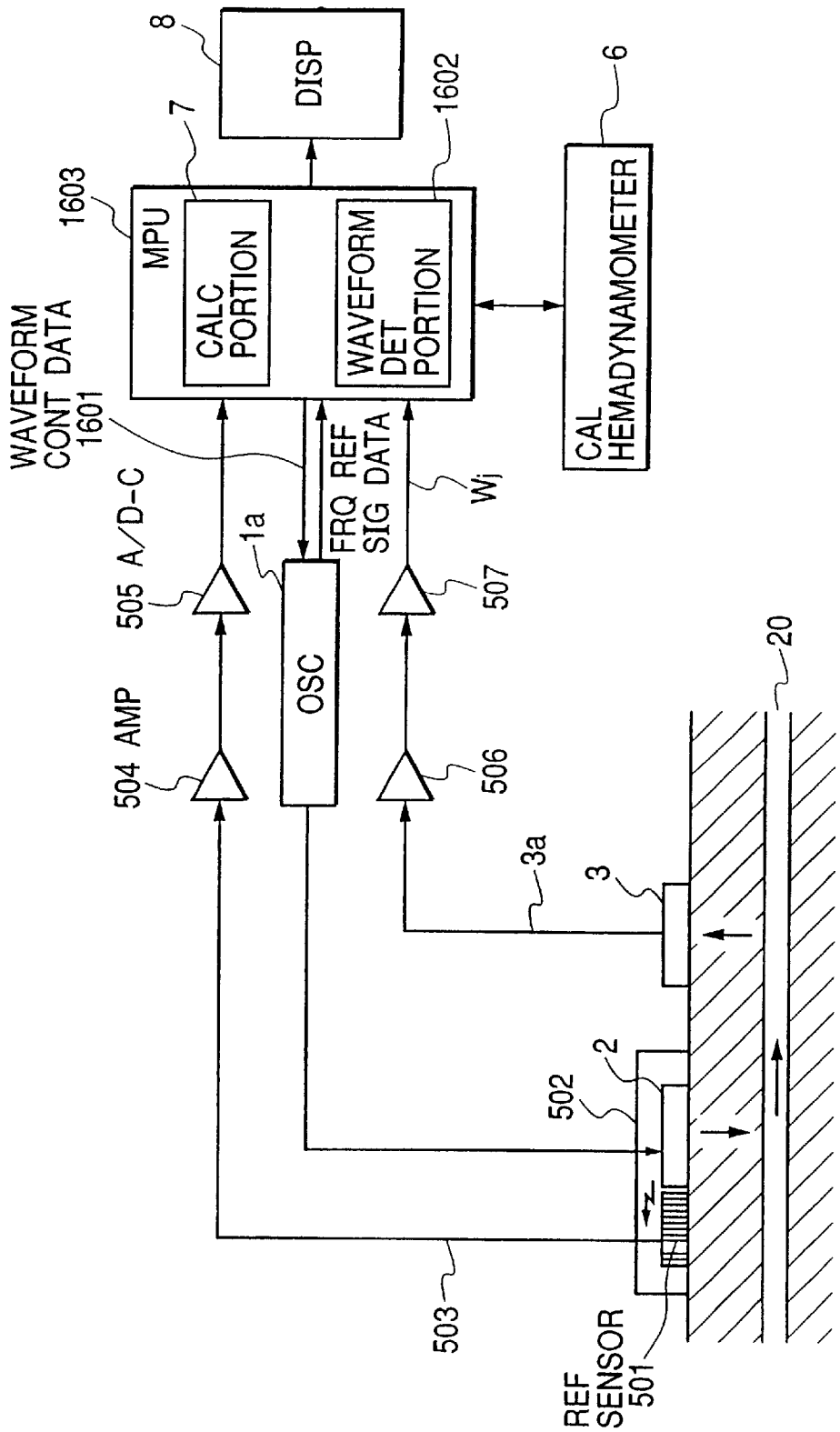
FIG. 19 is a block diagram of a noninvasive continuous blood pressure measuring apparatus of an eleventh embodiment of this invention.

FIG. 19 is a block diagram of a noninvasive continuous blood pressure measuring apparatus of an eleventh embodiment of this invention. The noninvasive continuous blood pressure measuring apparatus of the eleventh embodiment is substantially the same as that of the tenth embodiment. The difference is that the waveform determining portion 1602 is provided instead the frequency determining portion 509.

Figure 20:
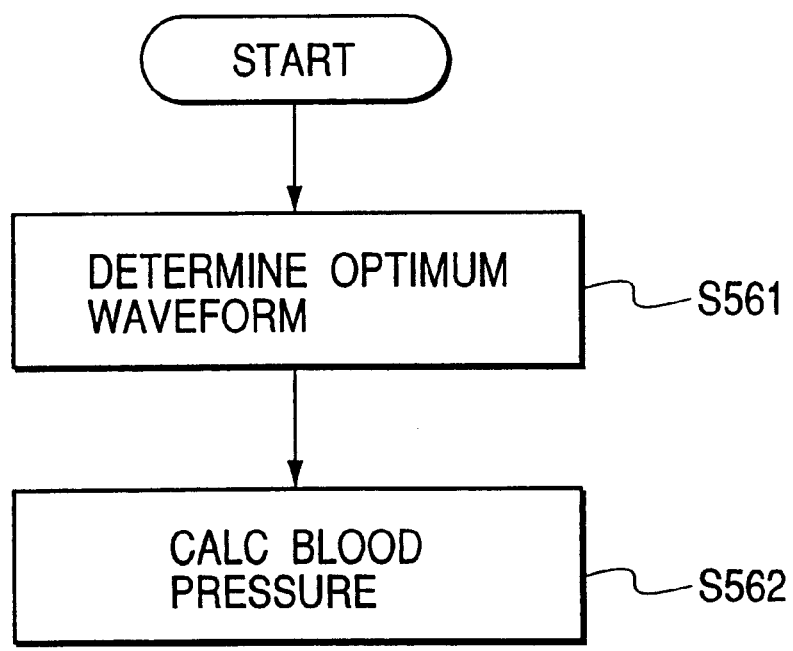
FIG. 20 depicts a flow chart of the eleventh embodiment showing an operation of the microprocessor.

FIG. 20 depicts a flow chart of the eleventh embodiment showing an operation of the microprocessor 1603.

Before detecting the continuous blood pressure, the waveform determining portion 1602 successively generates and supplies waveform control data 1601 indicative of a waveform Wj (j=1 to n) to the oscillator 1e for T seconds and successively detects the detection signal from the sensor 3 and the reference sensor detection signal 503 for the interval of T seconds to determine the optimum frequency and supplies the frequency control data indicative of the optimum waveform in step S561. When the optimum waveform has been determined, the microprocessor 1603 successively calculates the instantaneous blood pressure in step S562, so that the display 8 displays the continuous blood pressure variation from the successively supplied blood pressure from the calculation portion 7.

FIG. 21 depicts a flow chart of the eleventh embodiment showing an operation of the waveform determining portion 1602, that is, the step S561.

At first, the waveform determining portion 1602 generates the waveform control data indicative of a waveform Wj for the interval of T seconds in step S600. During the interval of T seconds, the oscillator 1e generates the oscillation signal having a waveform W1, for example Asin (2πft). The exciter 2 generates vibration of the waveform W1, so that the exciter waveform is induced in the artery 20.

In the following steps S601 to S605, the waveform estimation value is obtained as similar to the steps S501 to S505. The estimation value is given by:

$$Zwj = \alpha \cdot (Pwj/PStd) + \beta \cdot (RwjVar/RStd)$$

Then, processing returns to step S600 to generates the oscillation signal having a waveform wj.

The processing from steps S600 to S605 is repeated until j=n (n is a natural number).

Then, the waveform estimation values of W1 to Wn are obtained from the equation:

Then, in step S606, the optimum waveform showing the lowest waveform estimation value is selected. In the following step S607, the waveform determining portion 1602 supplies the waveform control data of the optimum waveform.

In this embodiment, the reference sensor 501 is used. However, this sensor can be omitted because the amplitude of the vibrations of the exciter 2 is substantially constant over waveform W1 to Wn. Moreover, it is possible that the amplitudes of the reference sensor detection signal with respect to waveforms W1 to Wn can be measured and stored in advance to be used in step S601.

What is claimed is:

1. A noninvasive continuous blood pressure measuring apparatus comprising:
   oscillating means for generating an oscillation signal having a desired frequency and a desired amplitude;
   an exciter arranged responsive to said oscillation signal for inducting an exciter waveform in an artery and blood in said artery of a living body;

a sensor arranged a predetermined interval apart from said exciter for receiving said induced exciter waveform transmitted through said artery from said living body and outputting a detection signal;

calibration hemadynamometer means for detecting absolute values of a maximum blood pressure and a minimum blood pressure of said living body;

calculating means for receiving absolute values from said calibration hemadynamometer means and successively calculating and outputting an instantaneous blood pressure value from a phase relation between said oscillation signal and said detection signal and said absolute values; and displaying means for displaying a continuous blood pressure variation from said instantaneous blood pressure successively outputted by said calculation means;

wherein said oscillation means further comprises:

clock signal generation means for generating a clock signal;

a processor responsive to frequency control data and said dock signal for successively generating frequency signal data indicative of amplitude in time base in accordance with said frequency control data;

a d/a converter for convening said frequency signal data; and filter means for low-pass filtering an output of said d/a converter and outputting said oscillation signal of which frequency is controlled in accordance with said frequency data.

* * * * *